United States Patent
Upton et al.

(10) Patent No.: US 10,570,436 B2
(45) Date of Patent: Feb. 25, 2020

(54) METHOD OF ANALYSING A SAMPLE INCLUDING A MICROORGANISM OF INTEREST

(71) Applicant: Spectromics Limited, Burford, Oxfordshire (GB)

(72) Inventors: Matthew Upton, Ivybridge (GB); Roy Goodacre, Stockport (GB)

(73) Assignee: Spectromics Limited c/o V J Hancock & Co., Ltd., Burford, Oxfordshire (GB)

( * ) Notice: Subject to any disclaimer, the term of this patent is extended or adjusted under 35 U.S.C. 154(b) by 195 days.

(21) Appl. No.: 15/120,665

(22) PCT Filed: Feb. 26, 2015

(86) PCT No.: PCT/GB2015/050551
§ 371 (c)(1),
(2) Date: Aug. 22, 2016

(87) PCT Pub. No.: WO2015/128650
PCT Pub. Date: Sep. 3, 2015

(65) Prior Publication Data
US 2017/0073725 A1 Mar. 16, 2017

(30) Foreign Application Priority Data
Feb. 26, 2014 (GB) .................................. 1403376.5

(51) Int. Cl.
*C12Q 1/18* (2006.01)
*G01N 21/33* (2006.01)

(52) U.S. Cl.
CPC .............. *C12Q 1/18* (2013.01); *G01N 21/33* (2013.01); *G01N 2201/129* (2013.01)

(58) Field of Classification Search
CPC ..... C12Q 1/18; G01N 21/33; G01N 2201/129
See application file for complete search history.

(56) References Cited

U.S. PATENT DOCUMENTS

| 4,847,198 A | 7/1989 | Nelson et al. | |
| 2005/0123917 A1 | 6/2005 | Labischinski et al. | |
| 2011/0143332 A1* | 6/2011 | Lin | G01N 21/658 435/5 |

FOREIGN PATENT DOCUMENTS

| WO | 9411526 A1 | 5/1994 |
| WO | 9914311 A1 | 3/1999 |
| WO | 9932656 A1 | 7/1999 |
| WO | 2012051437 A1 | 4/2012 |

OTHER PUBLICATIONS

Liu et al. PLoS ONE (2009) 4(5): e5470, pp. 1-10 (Year: 2009).*
Jain et a. (IEEE Transaction Pattern Analysis and Machine Intelligence (2000) 22(1): 4-37 (Year: 2000).*
Hadjigeorgiou et al. (Proc. SPIE 82290D: pp. 1-7, meeting: San Francisco, CA, Feb. 3, 2012 (Year: 2012).*
Kastanos et al. (Int. J. Spectroscopy (2012) Article ID 195317, pp. 1-13 (Year: 2012).*
Gaus et al. (Biopolymers (2006) 82: 286-290 (Year: 2006).*
Thi et al. (Proc. Spie 82290D: pp. 1-7, meeting: San Francisco, CA, Feb. 3, 2012 (Year: 2012).*
Defintion if infrared light from the Merriam-Webster website, https://www.merriam-webster.com/dictionary/infrared downloaded Feb. 3, 2018 (Year: 2018).*
Chen et al., Anal. Chem., 2010, vol. 82, No. 3, p. 1012-1019.*
ThermoFisher Scientific Catalog, NanoDrop 2000 Spectrophotometer, 4 pages of PDF, downloaded on Oct. 12, 2018.*
Goodacre et al., Microbiology, 1998, vol. 144, p. 1157-1170.*
Souto et al., Food Chemistry, 2010, vol. 119, Issue 1, p. 368-371.*
ISA/EP, International Search Report and Written Opinion for PCT Patent Application No. PCT/GB2015/050551, dated May 27, 2015.
Park, Chul Woo et al.: "Development of Rapid Assessment Method to Determine Bacterial Viability Based on Ultraviolet and Visible (UV-Vis) Spectroscopy Analysis Including Application to Bioaerosols", Aerosol and Air Quality Research, Apr. 25, 2012, XP055187979.
Peña-Gomar, Mary Carmen et al.: "Analysis of bacterial growth by UV/Vis spectroscopy and laser reflectometry", SPIE, 1000 20th St. Bellingham WA 98225-6705 USA, vol. 8412, Oct. 23, 2012, pp. 84120H-1-84120H-7, XP060026757.
Kaščáková, Slávka et al.: "Antibiotic Transport in Resistant Bacteria: Synchrotron UV Fluorescence Microscopy to Determine Antibiotic Accumulation with Single Cell Resolution", Plos One, vol. 7, No. 6, E38624, Jun. 12, 2012, pp. 1-9, XP055181989.
Lopez-Diez, E C. et al.: "Monitoring the Mode of Action of Antibiotics Using Raman Spectroscopy:? Investigating Subinhibitory Effects of Amikacin on Pseudomonas aeruginosa", Anal. Chem., vol. 77, 2005, pp. 2901-2906, XP002739439.
Espagnon, I. et al.: "Direct identification of clinically relevant bacterial and yeast microcolonies and macrocolonies on solid culture media by Raman spectroscopy", J. Biomed. Optics, vol. 19, 027004, Feb. 12, 2014, pp. 1-13, XP002739440.
WIPO, International Preliminary Report on Patentability for PCT Patent Application No. PCT/GB2015/050551, dated Aug. 30, 2016.

* cited by examiner

*Primary Examiner* — Kade Ariani
(74) *Attorney, Agent, or Firm* — NK Patent Law

(57) ABSTRACT

A method of analysing a sample including a microorganism of interest. The method includes exposing the sample to an antimicrobial; after exposing the sample to the antimicrobial, applying an absorption-based and/or scattering-based spectroscopic technique to the sample to obtain spectrum data whose spectral profile has been influenced by exposing the sample to the antimicrobial, wherein applying the absorption-based and/or scattering-based spectroscopic technique to the sample includes irradiating the sample with UV-Vis radiation; obtaining information regarding the susceptibility/resistance of the microorganism of interest to the antimicrobial from the spectrum data. The absorption-based and/or scattering-based spectroscopic technique may be applied to the sample no more than 60 minutes after the initial exposure of the sample to the antimicrobial. The method may be useful to obtain information regarding the susceptibility/resistance of a bacterium, such as a bacterium responsible for causing a UTI, to an antibiotic in a rapid and reliable manner.

17 Claims, 11 Drawing Sheets

METHOD OF ANALYSING A SAMPLE INCLUDING A MICROORGANISM OF INTEREST

FIELD OF THE INVENTION

This invention relates to a method of analysing a sample including a microorganism of interest. Preferably, the microorganism of interest is a bacterium, such as a bacterium responsible for causing a urinary tract infection ("UTI").

BACKGROUND

The inventors have observed that there is a clinical need for rapid and accurate diagnosis and treatment of infections. To meet this need, the inventors have observed that it would be useful for clinicians to be able to determine, rapidly and accurately, whether the microorganism causing the infection is sensitive to particular antibiotics, e.g. in order to treat patients appropriately, minimize their suffering and prevent potential complications from inappropriately treated infections, whilst at the same time reducing costs to healthcare organisations and the wider community.

Urinary tract infections ("UTIs") are a worldwide patient problem, particularly common in female patients, with 1 in 2 women experiencing a UTI at some point in their life[1,2]. It is predominantly caused by species of *Escherichia coli* ("*E. coli*") Millions of patients seek medical care in relation to UTIs every year, accounting for 1-3% of GP consultations in the UK every year[3].

Current methods of identifying the specific bacterium causing a UTI are very time-consuming. Typically, once a urine sample is provided by a patient, this sample is examined microscopically and cultured for 24 to 48 hours in the laboratory in order to identify the offending pathogenic organism(s). If an organism is identified, it usually takes the same amount of time to test the organism for its sensitivity to different antibiotics[3]. Because of this delay, initial treatment for UTIs is nowadays usually provided by clinicians on the basis of patient symptoms and/or a positive urine dipstick result and empirical treatment is prescribed using a broad spectrum antibiotic based on the presumed causative agent, most commonly *E. coli*[4-7]. This practice may lead to over-treatment (treatment given when no UTI is present), under-treatment (UTI not treated initially), or inappropriate treatment (ineffective antibiotic given). In addition, over the last two decades the emergence of antibiotic resistant strains of *E. coli* (up to 1 in 5 cases, and this is expected to rise) has made correct and fast diagnosis of UTI with rapid identification of the causative agent and its antibiotic sensitivities, of paramount importance[8-10].

The same issues of lengthy diagnosis and inappropriate treatment apply to conditions other than UTI, such as meningitis, pneumonia, sepsis and other infectious diseases.

The present invention has been devised in light of the above considerations.

SUMMARY OF THE INVENTION

The inventors have observed that there exist a variety of spectroscopic/spectrometric techniques that, when used with chemometrics/data analysis, could be a very powerful tool in rapidly identifying living organisms in biological mixtures[11-14]. Examples of such techniques include ultraviolet-visible ("UV-Vis") spectroscopy and vibrational spectroscopy techniques such as Raman spectroscopy, infrared spectroscopy and Fourier transform infrared spectroscopy.

Fourier transform infrared ("FT-IR") spectroscopy and other spectroscopic methods that use infrared radiation work by irradiating a sample with infrared ("IR") radiation causing a specific amount of radiation (which may be termed "light") to be absorbed by the organisms in the sample which is very specific to the structure of that organism[15]. This results in an IR fingerprint containing a huge amount of complex information which can then be simplified with the use of computer-based statistical techniques (chemometrics) and lead to the identification of that specific organism and the number of organisms in the sample[16].

The inventors have observed that a disadvantage of using FT-IR spectroscopy is that biological samples need to be dried prior to analysis in order to minimise interference from water. Also, samples should not be contained within low-cost plastic or glass cartridges or cuvettes that again would introduce interferences when FT-IR is used. Raman spectroscopy has a much weaker signal and also has issues with the inherent light scattering nature of many biological samples such as urine or blood, as Raman relies on light scattering as a means of analysis and this causes a means of sample-to-sample variation.

The present invention is based on a discovery by the present inventors that UV-Vis spectroscopy and other spectroscopic techniques (such as FT-IR and Raman) can be used to obtain a fast and accurate diagnosis of the susceptibility/resistance of bacteria responsible for causing UTIs (or other microorganisms) to antibiotics (or other antimicrobials) using a simple and inexpensive screening tool.

For most analytical applications used with organic materials, infrared spectroscopic techniques are usually thought to have significantly superior capability compared with other spectroscopic methods.

However, the inventors have found that experimental results obtained using UV-Vis spectroscopy are surprisingly useful in obtaining information regarding the susceptibility/resistance of a microorganism of interest to an antimicrobial, despite the perceived inferiority of UV-Vis spectroscopy compared with infrared spectroscopy techniques. In light of this discovery, the inventors believe that UV-Vis spectroscopy represents a particularly practical tool for obtaining information regarding the susceptibility/resistance of a microorganism of interest to an antimicrobial, since UV-Vis spectroscopy has various practical benefits (compared with infrared spectroscopic techniques) in that the sample does not require drying and can be analysed in situ, e.g. whilst in a plastic or glass container.

The present inventors have developed methods that use spectroscopic/spectrometric techniques in a manner that can allow information regarding the susceptibility/resistance of a microorganism of interest to an antimicrobial to be rapidly obtained, e.g. so as to help with guiding the prescription of effective antibiotics in clinical situations.

Although some of the experimental data described below relates to the microorganisms that are found in urine and are responsible for causing UTIs, as discussed below in more detail, the same principles/methods could equally be applied to other microorganisms, such as the microorganisms that cause infections in other bodily samples such as in blood, cerebral spinal fluid, sputum, joint fluid or nasal/vaginal/wound or other swabs; or such as microorganisms that colonise the body and may become infectious at a later date.

At its most general, a first aspect of the invention may provide:

A method of analysing a sample including a microorganism of interest, the method including:
exposing the sample to an antimicrobial;
after exposing the sample to the antimicrobial, applying a spectroscopic/spectrometric technique to the sample to obtain spectrum data whose spectral profile has been influenced by exposing the sample to the antimicrobial;

obtaining information regarding the susceptibility/resistance of the microorganism of interest to the antimicrobial from the spectrum data.

By such a method, the inventors have found that information regarding the susceptibility/resistance of the microorganism of interest to the antimicrobial can be obtained in a rapid and reliable manner.

In the context of this disclosure, applying a "spectroscopic/spectrometric technique" to a sample may include measuring a signal caused by performing an analytical technique on the sample as a function of a dependent variable.

Hence, in the context of this disclosure, "spectrum data" may be viewed as data representative of a measured signal caused by performing an analytical technique on a sample as a function of a dependent variable.

In the context of this disclosure, the "spectral profile" of spectrum data may be taken to mean the shape and/or variance of the spectrum data. In general, it is necessary for there to be multiple data points within a set of spectrum data in order for the spectrum data to have a spectral profile.

There are a wide range of spectroscopic/spectrometric techniques available to those skilled in the art. The terminology used to distinguish between spectroscopic techniques and spectrometric techniques is not always used consistently in the art, though "spectroscopic techniques" (which may be referred to under the umbrella term "spectroscopy") are usually understood to include measuring a signal caused by exposing a sample to radiated energy as a function of a dependent variable (usually, the radiated energy is electromagnetic radiation, though "spectroscopic techniques" that use other radiated energy, e.g. radiated pressure waves, are known).

Whilst the spectroscopic/spectrometric technique applied to the sample in the first aspect of the invention could be any one of the wide variety of spectroscopic/spectrometric techniques that are available (e.g. a mass spectrometry technique such as matrix assisted laser desorption ionisation, sometimes referred to as "MALDI"), the spectroscopic/spectrometric technique used (in a method according to the first aspect of the invention) is preferably an absorption-based and/or scattering-based spectroscopy technique.

Hence, the method preferably includes, after exposing the sample to the antimicrobial, applying an absorption-based and/or scattering-based spectroscopy technique to the sample to obtain spectrum data whose spectral profile has been influenced by exposing the sample to the antimicrobial.

Preferably, applying an "absorption-based and/or scattering-based spectroscopy technique" to a sample includes irradiating the sample with electromagnetic radiation and measuring absorption and/or scattering of the electromagnetic radiation by the sample, e.g. as a function of frequency or wavelength (or derivative thereof), to obtain the spectrum data. In this case, the spectrum data would be representative of absorption and/or scattering by the sample measured, for example, as a function of frequency or wavelength of the electromagnetic radiation (any units may be used).

In some embodiments, the spectroscopic technique may be an absorption-based spectroscopy technique. Applying an "absorption-based spectroscopy technique" to a sample may include irradiating the sample with electromagnetic radiation and measuring absorption of the electromagnetic radiation by the sample, e.g. as a function of frequency or wavelength, to obtain the spectrum data. In this case, the spectrum data would be representative of absorption by the sample measured, for example, as a function of frequency or wavelength (or derivative thereof) of the electromagnetic radiation (any units may be used).

In some embodiments, the spectroscopic technique may be a scattering-based spectroscopy technique. Applying a "scattering-based spectroscopy technique" to a sample may include irradiating the sample with electromagnetic radiation and measuring scattering of the electromagnetic radiation by the sample, e.g. as a function of frequency or wavelength, to obtain the spectrum data. In this case, the spectrum data would be representative of scattering by the sample measured, for example, as a function of frequency or wavelength (or derivative thereof) of the electromagnetic radiation (any units may be used).

Preferably, applying the absorption-based and/or scattering-based spectroscopy technique to the sample includes irradiating the sample with UV-Vis and/or IR radiation (i.e. electromagnetic radiation in the ultraviolet-visible and/or infrared spectral regions).

Examples of absorption-based spectroscopy techniques that include irradiating a sample with infrared radiation include Fourier transform infrared ("FT-IR") spectroscopy (in which a Fourier transform is applied to the measurements), attenuated total reflectance ("ATR") and dispersive infrared spectroscopy.

An example of a scattering-based spectroscopy technique that includes irradiating a sample with infrared radiation is Raman spectroscopy, in which scattering is measured to obtain information regarding the vibrational modes of a system.

Any absorption-based and/or scattering-based spectroscopic technique that uses UV-Vis radiation may be referred to herein as "UV-Vis spectroscopy". In many current applications (and in the experimental work described below with reference to FIG. 9 and FIG. 10), UV-Vis spectroscopy is performed as an absorption-based technique, but the inventors note that measuring multi-angle scattering and/or absorbance of UV-Vis radiation could also be useful in the context of this invention.

Surprisingly, the inventors have found that useful information regarding the susceptibility/resistance of the microorganism of interest can be obtained from spectrum data obtained by applying an absorption-based and/or scattering-based spectroscopy technique, wherein applying the absorption-based and/or scattering-based spectroscopy technique to the sample includes irradiating the sample with UV-Vis and/or IR radiation, even if the absorption-based and/or scattering spectroscopy technique is applied to the sample very soon after exposure of the sample to the antimicrobial. For example, as discussed below, the inventors have found that useful information can be obtained from spectroscopy measurements performed as soon as 10 minutes after addition of the antimicrobial.

The inventors have been particularly surprised at the high quality of results that have been obtained by irradiating a sample with UV-Vis radiation (see e.g. FIG. 9 and FIG. 10) soon (e.g. as short as 10 minutes) after exposure of the sample to the antimicrobial, which the inventors have found to be of comparable standard to results obtained by FT-IR (see e.g. FIG. 7). One reason for the inventors being surprised by the UV-Vis results is that UV-Vis spectroscopy is usually seen as providing considerably less chemical information relating to structural and physical characteristics compared with IR-based techniques (such as FT-IR and Raman) which measure molecular vibrations from chemical functional groups. By contrast, UV-Vis spectroscopy is usually used to provide information on the colour of the chemicals in the sample by absorption or scattering the light.

Such chromophores include (but are not limited to) proteins, DNA, RNA and many other pigmented (bio-)chemicals. The inventors believe the results obtained using UV-Vis spectroscopy to be a particularly promising, since the inventors have observed that there are key benefits of UV-Vis spectroscopy compared with IR spectroscopic techniques. For example, a key benefit of UV-Vis spectroscopy over IR spectroscopic techniques is that a liquid sample can be tested without the need for drying. Also, with UV-Vis spectroscopy, a liquid sample can be contained in a closed tube made of transparent plastic or glass.

Therefore, in some embodiments, applying the absorption-based and/or scattering-based spectroscopy technique to the sample preferably includes irradiating the sample with UV-Vis radiation.

In other embodiments, applying the absorption-based and/or scattering-based spectroscopy technique to the sample may include irradiating the sample with IR radiation.

Typically, ultraviolet-visible ("UV-Vis") radiation is taken to be electromagnetic radiation having a wavelength in the range 1 nm to 750 nm, where ultraviolet radiation is taken to be electromagnetic radiation having a wavelength in the range 1 nm to 400 nm, and where visible radiation is taken to be electromagnetic radiation having a wavelength in the range 400 nm to 750 nm. Therefore, the absorption-based and/or scattering-based spectroscopy technique may use UV-Vis radiation in the range 1 nm to 750 nm.

However, for the purposes of this disclosure, UV-Vis is preferably taken to be electromagnetic radiation having a wavelength in the range 1 nm to 800 nm, since the inventors have found that electromagnetic radiation falling within this range can be particularly useful. Therefore, the absorption-based and/or scattering-based spectroscopy technique preferably uses UV-Vis radiation in the range 1 nm to 800 nm.

Typically, infrared ("IR") radiation may be taken to be electromagnetic radiation having a wavelength in the range 750 nm to 1 mm. Therefore, the absorption-based and/or scattering-based spectroscopy technique may use IR radiation in the range 750 nm to 1 mm.

The absorption/scattering-based spectroscopy technique may use electromagnetic radiation having a wavelength in the range 1 nm to 1 mm, since this range covers radiation in both the IR and UV-Vis spectral regions, which are both thought to be useful in the context of the invention.

The inventors have found that for the purposes of the present invention, it is particularly preferred for the absorption/scattering-based spectroscopy technique to use UV-Vis radiation having a wavelength in the range 200 nm to 800 nm, more preferably in the range 300 nm to 800 nm (300 nm to 800 nm was the range of wavelengths used to produce the data shown in FIG. 9). Therefore, the absorption-based and/or scattering-based spectroscopy technique preferably uses UV-Vis radiation in the range 200 nm to 800 nm, and more preferably uses UV-Vis radiation in the range 300 nm to 800 nm.

Herein, where it is stated that it is a spectroscopy technique uses electromagnetic radiation in a stated range of wavelengths/frequencies (e.g. in the range 300 nm to 800 nm, as above), the spectroscopic technique preferably uses electromagnetic radiation falling at least partially within the stated range, and more preferably uses electromagnetic radiation covering 50% or more of (more preferably 75% or more of) the stated range. So, for example, a spectroscopic technique using electromagnetic radiation between 199 nm and 650 nm would be considered as a spectroscopic technique that uses UV-Vis radiation between 200 nm and 800 nm, since 199 nm and 650 nm covers 200 nm to 650 nm (which is 75% of the range 200 nm to 800 nm).

For the avoidance of any doubt, a spectroscopic technique using electromagnetic between two given wavelengths/frequencies (e.g. 199 nm and 650 nm, as above) may be considered as covering a range of wavelengths/frequencies (e.g. 200 nm to 650 nm, as above), even if the spectroscopic technique uses only a selection of discrete wavelengths/frequencies (rather than a continuum of wavelengths/frequencies) between the two given wavelengths/frequencies.

The invention is exemplified below using both UV-Vis and FT-IR spectroscopy.

Nonetheless, the inventors believe that the invention should also work with other absorption-based and/or scattering-based spectroscopy techniques that use electromagnetic radiation falling both inside and outside of the IR and UV-Vis spectral regions, because these techniques will similarly provide chemical information of the sample under analysis.

The inventors also believe that the invention should also work with other spectroscopic/spectrometric techniques (e.g. MALDI mass spectrometry), because these techniques will also provide chemical information of the sample under analysis.

Exposing the sample to an antimicrobial may include adding a quantity of the antimicrobial to the sample.

Exposing the sample to the antimicrobial may further include mixing the sample after adding a quantity of the antimicrobial to the sample, e.g. so as to help disperse the antimicrobial homogeneously within the sample.

The method may further include any one or more of the following steps: adding a growth media to the sample, adding a buffer to the sample, maintaining the sample at a predetermined temperature (e.g. at or close to 37.5° C.), adding a nutrient to the sample. Such steps may be useful to help maintain the viability of the microorganism during the method of analysis.

Preferably, the quantity of antimicrobial added to the sample is large enough to significantly influence the spectral profile of the spectrum data. The quantity required to achieve this will vary depending on the microorganism and antimicrobial concerned, therefore prescribing a specific quantity of antimicrobial in this document is not desirable. Nonetheless, by way of non-limiting example, the quantity of antimicrobial added to the sample may be at least 10% of the minimum inhibitory concentration of the antimicrobial, and is more preferably at least 100% of the minimum inhibitory concentration of antimicrobial, and is more preferably 100%-400% of the minimum inhibitory concentration of the antimicrobial.

Minimum inhibitory concentration ("MIC") is a widely used term in microbiology, and is typically used to describe the lowest concentration of a given antimicrobial that will inhibit the visible growth of a given microorganism of interest after overnight incubation. The MIC is therefore an experimentally determined concentration that is specific to a given microorganism in relation to a given antimicrobial.

In conventional methods, an indication of whether a given microorganism is susceptible or resistant to a given antimicrobial may be obtained by obtaining a minimum inhibitory concentration ("MIC") for that microorganism in relation to that antimicrobial, and comparing the MIC with a breakpoint concentration. The "breakpoint concentration" is a predetermined value that is typically determined following regression analysis of large collections of wild type isolates. The breakpoint concentration for a given antimicrobial may be viewed as a predetermined cut-off value, which may represent a therapeutically achievable antimicrobial concentration. Microorganisms with an MIC above this cut-off value may be defined as being resistant to the antimicrobial and microorganisms with an MIC below this cut-off value may be defined as being susceptible to the antimicrobial. The extent to which an MIC differs from a breakpoint concentration may provide a numerical indication of the extent to which a given microorganism is susceptible or resistant to a given antimicrobial.

In general, there will usually be a time gap between exposing the sample to the antimicrobial and applying the absorption-based spectroscopic technique to the sample. The inventors have observed that this time gap ought to be long enough for the spectrum data to be adequately influenced by exposing the sample to the antimicrobial so that useful information regarding the susceptibility/resistance of the microorganism of interest to the antimicrobial can be obtained from the spectrum data. However, from a clinical perspective, the sooner that information regarding the susceptibility/resistance of the microorganism of interest to the antimicrobial can be obtained, the better.

Accordingly, the inventors observe that the time gap between exposing the sample to the antimicrobial and applying the absorption-based spectroscopic technique to the sample is preferably chosen to be as short as possible, whilst still allowing for useful information regarding the susceptibility/resistance of the microorganism of interest to the antimicrobial to be obtained.

Surprisingly, the inventors have found that it is possible to obtain useful information regarding the susceptibility/resistance of a microorganism of interest to an antimicrobial, even if the time gap between exposing the sample to the antimicrobial and applying the spectroscopic/spectrometric technique to the sample is very short.

For example, the experimental data set out below shows that, for an absorption-based spectroscopic technique, useful information regarding the susceptibility/resistance of a microorganism of interest to an antimicrobial can be obtained with a time gap of as small as 10 minutes (see e.g. Table 6, below), which may for example allow useful clinical information to be obtained in a typical clinical setting (e.g. within a patient's appointment with a doctor or at a patient's bedside in a clinical setting).

The inventors are not sure why information regarding the susceptibility/resistance of a microorganism of interest to an antimicrobial can be obtained by applying a spectroscopic technique so soon after exposing the sample to the antimicrobial, given that the time periods involved would not normally be adequate to allow significant population growth of the microorganism of interest. Without wishing to be bound by theory, the inventors think that this may be because the microorganism of interest is modifying itself very rapidly due to the new stress condition that it is under (i.e. due to exposing the sample to the antimicrobial) and that this modification is at the phenotypic level and results in a change in the biochemical composition of some unknown part(s) of the microorganism of interest.

In view of these considerations, the spectroscopic/spectrometric technique (which may be an absorption-based and/or scattering-based spectroscopic technique, see above) is preferably applied to the sample no more than 360 minutes after, more preferably no more than 240 minutes after, more preferably no more than 180 minutes after, more preferably no more than 120 minutes after, more preferably no more than 90 minutes after, more preferably no more than 75 minutes after, more preferably no more than 60 minutes after, more preferably no more than 30 minutes after, more preferably no more than 20 minutes after, more preferably no more than 15 minutes after, more preferably no more than 10 minutes after, more preferably no more than 5 minutes (or even sooner) after, the initial exposure of the sample to the antimicrobial.

For the avoidance of any doubt, the spectroscopic/spectrometric technique may be applied to the sample before the sample is exposed to the antimicrobial (i.e. in addition to the spectroscopic technique being applied to the sample after the sample is exposed to the antimicrobial). Accordingly, in some embodiments, the method may include:

before and after exposing the sample to the antimicrobial, applying a spectroscopic/spectrometric technique to the sample to obtain spectrum data whose spectral profile has been influenced by exposing the sample to the antimicrobial.

In this case, spectrum data obtained from applying the spectroscopic/spectrometric technique to the sample before the sample is exposed to the antimicrobial may be referred to as "pre-exposure" spectrum data and spectrum data obtained from applying the spectroscopic/spectrometric technique to the sample after the sample is exposed to the antimicrobial may be referred to as "post-exposure" spectrum data, for clarity.

In some embodiments, the method may therefore include:

before and after exposing the sample to the antimicrobial, applying a spectroscopic/spectrometric technique to the sample to obtain delta (i.e. "difference") spectrum data whose spectral profile has been influenced by exposing the sample to the antimicrobial, wherein the delta spectrum data represents post-exposure spectrum data relative to pre-exposure spectrum data.

However, note that a step of applying the spectroscopic/spectrometric technique before the sample is exposed to the antimicrobial is not a requirement of the invention, since such a step is not required to obtain information regarding the susceptibility/resistance of the microorganism of interest to the antimicrobial from the spectrum data (or spectral profile data obtained from the spectrum data). For example, information regarding the susceptibility/resistance of the microorganism of interest to the antimicrobial from the spectrum data (or spectral profile data obtained from the spectrum data) may be obtained from:

spectrum data that represents post-exposure spectrum data relative to spectrum data obtained by applying the spectroscopic technique to a control sample; or spectrum data that represents post-exposure spectrum data without reference to another set of spectrum data.

Thus, it should be apparent that the spectrum data may represent post-exposure spectrum data relative to another set of spectrum data or may represent the post-exposure spectrum data without reference to another set of spectrum data.

By way of example, if the spectrum data represents the post-exposure spectrum data relative to another set of spectrum data, the other set of spectrum data may be:

spectrum data obtained by applying the spectroscopic technique to the sample before the sample was exposed to the antimicrobial; or spectrum data obtained by applying the spectroscopic technique to a control sample including the microorganism of interest, wherein the control sample has not been exposed to the antimicrobial when the spectroscopic technique was applied to it.

As noted above, in the case that the spectrum data represents the post-exposure spectrum data relative to pre-exposure spectrum data, the spectrum data may be referred to as "delta" spectrum data.

For the avoidance of any doubt, the spectroscopic/spectrometric technique may be applied at different time intervals after exposing the sample to the antimicrobial (e.g. at 1 minute time intervals after exposing the sample to the antimicrobial), e.g. so that the change in spectrum data (or spectral profile data obtained from the spectrum data) with time can be observed (see e.g. FIG. 8, discussed below).

Preferably, the information regarding the susceptibility/resistance of the microorganism of interest to the antimicrobial includes an indication of whether the microorganism is susceptible or resistant to the antimicrobial. As discussed in more detail below, this indication may be obtained, for example, by applying a model to spectral profile data obtained from the spectrum data.

For the avoidance of any doubt, the indication of whether the microorganism is susceptible or resistant to the antimicrobial might not be 100% accurate. However, the experimental work section below shows that surprisingly high levels of accuracy can be obtained, even if the spectroscopic/spectrometric technique is applied to the sample very soon after exposure of the sample to the antimicrobial.

The information regarding the susceptibility/resistance of the microorganism of interest to the antimicrobial may (additionally or alternatively) include an indication of the extent to which the microorganism of interest is susceptible or resistant to the antimicrobial. This indication could be obtained, for example, by comparing the spectrum data (directly or indirectly) with reference spectrum data obtained by exposing samples containing reference microorganisms of known MIC values to the same antimicrobial. Note that this indication would most likely be provided in qualitative (rather than quantitative) form, since the MIC of the microorganism of interest might not be known (as noted above, an MIC is usually required to obtain a numerical indication of the extent to which a given microorganism is susceptible or resistant to a given antimicrobial).

Of course, an indication of whether the microorganism is susceptible or resistant to the antimicrobial (and, if applicable, an indication of the extent to which the microorganism of interest is susceptible or resistant to the antimicrobial), if obtained in a quick and reliable manner, would potentially be of use in a clinical environment, e.g. in assessing which antibiotic to treat a patient with a UTI.

Preferably, the information regarding the susceptibility/resistance of the microorganism of interest to the antimicrobial includes an indication of a mechanism of resistance of the microorganism to the antimicrobial. As discussed in more detail below, this indication may be obtained, for example, from a cluster plot of spectral profile information obtained from the spectrum data.

Such an indication, particularly if it could be obtained in a quick and reliable manner, would potentially be of use in a research environment, e.g. in screening for efficacy of new candidate drugs that function via a preferred mode of action, or in screening for clinical trial subjects that have microbial infections that are susceptible, or resistant to antimicrobials with certain modes of action.

A skilled person would appreciate that there are a variety of different ways in which information regarding the susceptibility/resistance of the microorganism of interest to the antimicrobial may be obtained from the spectrum data.

In some embodiments, the information regarding the susceptibility/resistance of the microorganism of interest to the antimicrobial may be obtained directly from the spectrum data itself.

For example, the information regarding the susceptibility/resistance of the microorganism of interest to the antimicrobial may be obtained using an algorithm configured to provide information regarding the susceptibility/resistance of the microorganism of interest to the antimicrobial directly from spectrum data.

Such an algorithm may, for example, use:
- a database containing reference spectrum data, e.g. obtained by exposing samples containing reference microorganisms of known susceptibility/resistance to the antimicrobial; and/or
- a "look up" table configured to transpose spectrum data to provide information regarding the susceptibility/resistance of the microorganism of interest to the antimicrobial, e.g. as a qualitative result.

The database may include reference spectrum data obtained as described below with reference to the second aspect of the invention, for example.

Similarly, reference spectrum data obtained as described below with reference to the second aspect of the invention may have been used to produce the look up table.

In other embodiments, the information regarding the susceptibility/resistance of the microorganism of interest to the antimicrobial may be obtained indirectly from the spectrum data, e.g. as will now be explained with reference to spectral profile data.

Preferably, obtaining information regarding the susceptibility/resistance of the microorganism of interest to the antimicrobial from the spectrum data includes:
- using multiple data points within the spectrum data to obtain spectral profile data which represents the spectral profile of the spectrum data; and
- obtaining information regarding the susceptibility/resistance of the microorganism of interest to the antimicrobial from the spectral profile data.

By way of example, the spectral profile data may be obtained according to a computational technique, with the multiple data points within the spectrum data being used as inputs for the computational technique.

The computational technique according to which the spectral profile data is obtained may be an unsupervised computational technique.

An "unsupervised" computational technique may be understood herein to mean a computational technique that is performed without using labelled training data (see below for a definition of labelled training data). An example of an "unsupervised" computational technique is principal component analysis ("PCA"), although there are many algorithms that use unsupervised learning principles.

Accordingly, the spectral profile data may be obtained according to PCA, with the multiple data points within the post-exposure spectrum data being used as inputs for the PCA.

However, as would be appreciated by a skilled person, the spectral profile data is obtained according to a variety of different unsupervised computational techniques, not just PCA.

The computational technique may in some embodiments be a statistical technical (PCA is an example of a statistical technique), but of course, the spectral profile data could be obtained using a computational technique that does not necessarily use statistics.

It should also be understood that the steps of obtaining spectral profile data and obtaining information from the spectral profile data are not required e.g. since, as noted above, information regarding the susceptibility/resistance of the microorganism of interest to the antimicrobial could be obtained directly from the spectrum data itself.

In some embodiments, the information regarding the susceptibility/resistance of the microorganism of interest to the antimicrobial may be obtained from spectral profile data that is represented on a cluster plot, e.g. by comparing the spectral profile data on the cluster plot with reference spectral profile data (which may e.g. be plotted on the same cluster plot or on a separate cluster plot). The reference spectral profile data may have been obtained by exposing samples containing reference microorganisms of known susceptibility/resistance to the antimicrobial. The reference spectrum data may have been obtained as described below with reference to the second aspect of the invention.

An example cluster plot from which information regarding the susceptibility/resistance of a microorganism of interest to an antimicrobial may be obtained is discussed below with reference to FIG. 7, in which different microorganisms exposed to the same antimicrobial are located in different places in these plots after antimicrobial exposure, yet all the microorganisms clustered together before exposure to the antimicrobial. Note that microorganisms with the same mode of resistance cluster together after exposure to the antimicrobial, showing that the same change in spectral profile reflects the mechanism (or "mode") of antimicrobial resistance. This demonstrates that an indication of a mechanism of resistance of a microorganism to an antimicrobial could be obtained from a cluster plot.

Preferably, the information regarding the susceptibility/resistance of the microorganism of interest to the antimicrobial is obtained from the spectral profile data by applying a model to the spectral profile data. The model is thus preferably configured to be applied to spectral profile data to obtain information regarding the susceptibility/resistance of the microorganism of interest to the antimicrobial.

Preferably, the model (that is applied to the spectral profile data to obtain information regarding the susceptibility/resistance of a microorganism of interest to the antimicrobial) is a "supervised" model that has been produced using labelled training data.

In general, labelled training data may be understood as data representing observations, wherein each observation is accompanied by a respective label which classifies the observation. Methods of modelling data using labelled training data are well known.

The model may be a mathematical model, e.g. a statistical model. However, non-statistical machine learning could also be employed. The important aspect is that the model preferably uses labelled training data and is therefore supervised.

Thus, in the case that labelled training data are used to produce a supervised model (that is applied to the spectral profile data to obtain information regarding the susceptibility/resistance of a microorganism of interest to the antimicrobial), the labelled training data preferably includes items of previously acquired spectral profile data, wherein each item of previously acquired spectral profile data:

was obtained by exposing a sample including a known microorganism to an antimicrobial; and
is accompanied by a respective label which classifies the item of previously acquired spectral profile data to provide information regarding the susceptibility/resistance of the known microorganism to the antimicrobial.

Thus, the labelled training data may be reference spectral profile data obtained as described below with reference to the second aspect of the invention, for example.

The supervised model may, for example, be produced according to discriminant analysis (herein we exemplify this using discriminant function analysis ("DFA"), but other algorithms could be performed in a very similar manner) and/or partial least squares-discriminant analysis ("PLS-DA"). However, as would be appreciated by a skilled person, the model may be produced according to a variety of different analyses, not just DFA or PLS-DA.

The supervised model may form part of a database. The database may function as a "look up" table. The database may contain reference spectrum data obtained by exposing samples containing reference microorganisms of known susceptibility/resistance to the antimicrobial.

A skilled person would, based on the teaching of this document, find no difficulty in forming a model (e.g. a supervised model such as a DFA or PLS-DA model) that could be applied to spectral profile data to obtain information regarding the susceptibility/resistance of the microorganism of interest to the antimicrobial, e.g. so as to obtain an indication of whether the microorganism is susceptible or resistant to the antimicrobial, or to obtain an indication of a mechanism of resistance of the microorganism to the antimicrobial. Such models are exemplified in the experimental work below, see e.g. Tables 3, 5 and 6.

The microorganism included in the sample may be a microorganism responsible for causing an infection, such as a UTI.

An infection may be any infection or infectious disease, e.g. bacterial, viral, fungal, or parasitic infection.

The microorganism may be a pathogen responsible for causing a disease.

Preferably, the microorganism included in the sample is a bacterium, such as a bacterium responsible for causing a UTI.

The bacterium may be a Gram-negative bacterium. Gram-negative bacteria may be defined as a class of bacteria that do not retain the crystal violet stain used in the Gram staining method of bacterial differentiation, making positive identification possible.

Example Gram-negative bacteria include proteobacteria or bacteria of the family Enterobacteriaceae, such as *Escherichia coli, Enterobacter* spp., *Proteus* spp., *Salmonella* spp., *Shigella* spp., *Klebsiella* or bacteria selected from the genus *Acinetobacter, Pseudomonas, Helicobacter, Neisseria, Legionella, Haemophilus* or *Yersinia*.

The bacterium may belong to the Enterobacteriaceae family of bacteria. The Enterobacteriaceae family is a well-known large family of Gram-negative bacteria.

In some examples, the microorganism may be an *E. coli* bacterium. This is an example of a Gram-negative class of bacteria as well as an example of an Enterobacteriaceae.

The bacterium may be a Gram-positive bacterium. Gram-positive bacteria may be defined as a class of bacteria that do retain the crystal violet stain used in the Gram staining method of bacterial differentiation, making positive identification possible.

Example Gram-positive bacteria include bacteria from the bacillus or coccus groups, optionally bacteria from the genera Bacillus, *Enterococcus, Listeria, Clostridium* (e.g. *C. difficile*), *Staphylococcus* (e.g. *S. aureus*), or *Streptococcus*.

The bacterium may be a Gram-variable bacterium. Gram-variable bacteria can be understood as bacteria that do not respond predictably to the Gram staining method of bacterial differentiation. Example Gram-variable bacteria may include *Mycobacteria, Mycoplasma, Chlamydia*.

The experimental work set out below demonstrates that the method can be performed on a wide variety of bacteria.

Preferably, the antimicrobial is an antibacterial. This may be appropriate if the microorganism is a bacterium.

Preferably, the antibacterial is an antibiotic, which is a subset of antibacterials.

An antibiotic may be defined as a substance that either kills microorganisms (e.g. a bacteriocidal agent) or inhibits/stops growth of microorganisms (e.g. a bacteriostatic agent).

For the avoidance of any doubt, antibiotics may include compounds that are typically useful in treating microbial infections, not limited to bacterial infections.

An example of an antibacterial that is not an antibiotic would be a disinfectant, e.g. as may be used in a mouthwash.

Antibiotics are commonly classified according to their mechanism of action. For example, the antibiotic may have a mechanism of action: that targets a bacterial cell wall (e.g. the penicillin and cephalosporin classes of antibiotics have this mechanism of action), that interferes with bacterial enzymes (e.g. the sulfonamide class has this mechanism of action), and/or that targets protein synthesis (e.g. the aminoglycoside class has this mechanism of action). Additionally/alternatively, the antibiotic may have a mechanism of action that targets a bacterial cell membrane (e.g. the polymyxin class of antibiotics has this mechanism of action), Examples of antibiotics include β-lactam antibiotics (e.g. penicillin, ampicillin), cephalosporins (cefacetril, cefradin), carbapenems (e.g. imipenem, meropenem), which generally cause cell death by degradation of the cell wall; aminoglycosides (e.g. amikacin, kanamycin, neomycin), macrolides (e.g. azithromycin, erythromycin), lincosamides (e.g. lincomycin), tetracylines (e.g. tetracycline) or oxazolidinones (e.g. 2-Oxazolidone) which generally act to inhibit protein synthesis thereby exerting a cytostatic effect; enzyme inhibitors (e.g. trimethoprim and sulfonamides); agents that interfere with DNA stability, replication or maintenance such as quinolones (e.g. fluoroquinolones, ciprofloxacin).

In some examples, the antibiotic may belong to the aminoglycoside class (Amikacin is an example belonging to this class), the penicillin class (Ampicillin is an example belonging to this class) or the sulfonamide class (Trimethoprim is an example belonging to this class) of antibiotic.

The method may be useful to obtain information regarding the susceptibility/resistance of a bacterium, such as a bacterium responsible for causing a UTI, to an antibiotic in a rapid and reliable manner.

In other embodiments, the microorganism included in the sample may be a viral microorganism (such as influenza), a fungal microorganism (such as *candida*) or a parasitic microorganism (such as protozoa). These microorganisms are all common causes of infectious diseases, and can be treated with antimicrobials (e.g. to kill the microorganisms or to stop/inhibit growth of the microorganisms).

Example viral microorganisms include influenza virus, measles virus, hepatitis B virus (HBV), hepatitis C virus (HCV), human immunodeficiency virus (HIV), Herpes simplex virus and human papilloma virus.

Example fungal microorganisms include *Alternaria* spp., *Aspergillus* spp., *Candida* spp., *Cryptococcus* spp., *Pneumocystis* spp. and *Histoplasma* spp. A fungal infection may be fungal sepsis or histoplasmosis.

Example parasitic microorganisms include protozoa such as *Plasmodium* species (e.g. *Plasmodium falciparum, Plasmodium yoeli, Plasmodium ovale, Plasmodium vivax,* or *Plasmodium chabaudi*), helminths such as the parasitic cestode, trematode or nematode worms and ectoparasites. A parasitic infection may be a disease such as malaria, leishmaniasis and toxoplasmosis.

Similarly, the antimicrobial may be an antiviral (which may be appropriate if the microorganism in the sample is a viral microorganism), an antifungal (which may be appropriate if the microorganism in the sample is a fungal microorganism) or an antiparasitic (which may be appropriate if the microorganism in the sample is a parasitic microorganism).

The microorganism may be a cellular microorganism (e.g. a bacterium, a fungal microorganism or a parasitic microorganism) or a non-cellular microorganism (e.g. a viral microorganism).

For the avoidance of any doubt, the term microorganism encompasses viral microorganisms (such as influenza) for the purpose of this disclosure.

The method may be performed on a sample that includes or derives from material obtained from a patient, wherein the material obtained from the patient includes the microorganism of interest.

The sample may be liquid.

A sample may be taken from any tissue or bodily fluid, e.g. from a non-human mammal or from a human. The sample may comprise or may be derived from: a quantity of blood; a quantity of urine; a quantity of serum derived from the individual's blood which may comprise the fluid portion of the blood obtained after removal of the fibrin clot and blood cells; a quantity of pancreatic juice; a tissue sample or biopsy; or cells isolated from said individual. For the avoidance of any doubt, the sample could be plasma (which, for example, may have blood cells removed but clotting factors left in) or cerebrospinal fluid ("CSF").

The method may be performed as an in vitro method.

The sample may be an uncultured sample. Herein, an uncultured sample may be defined as a sample in which a microorganism of interest has not been grown in an artificial culture (e.g. prior to exposure to the antimicrobial).

Performing the method on an uncultured sample may be desirable in a clinical environment, where preparing a cultured sample uses up time and resources.

In some embodiments, the method may be performed on an uncultured urine sample obtained from a patient. In general, an uncultured urine sample from a patient will, if it includes any bacteria at all, include at most one dominant bacterium, so applying the method on such a urine sample (e.g. to obtain information regarding the susceptibility/resistance of the dominant bacterium) would be straightforward in most cases.

If multiple bacteria were present in significant quantities in the uncultured urine sample, it would be possible to isolate/culture each bacterium before performing the method on each bacterium. However, a sample containing a mixture of more than one microorganism may give a spectral profile that can be interpreted to allow selection of an appropriate antimicrobial to allow treatment of either all microorganisms present or a dominant microorganism, without there being a need to separate out the individual microorganisms from the mixture.

In other embodiments, the sample may be a cultured sample, which has been grown in an artificial culture (e.g. prior to exposure to the antimicrobial).

The method may include:
  obtaining material from a patient, wherein the material includes the microorganism of interest; and
  preparing the sample using the material obtained from a patient.

For the avoidance of any doubt, the steps of obtaining material from a patient and preparing the sample are optional and may be disclaimed.

A skilled person will appreciate from the present disclosure that, in order to perform a method of analysing a sample including a microorganism of interest according to the first aspect of the invention, it will usually be necessary for some pre-analysis to have been performed on microorganisms having biochemical properties which are related to those of the microorganism of interest.

Thus, a second aspect of the invention may provide: A pre-analysis method for use in subsequently obtaining information regarding the susceptibility/resistance of a microorganism of interest to an antimicrobial, the pre-analysis method including:

providing a plurality of reference samples, wherein each reference sample includes a respective reference microorganism, wherein each reference microorganism is of known susceptibility/resistance to the antimicrobial and has biochemical properties which are related to those of the microorganism of interest;

for each reference sample:
exposing the reference sample to the antimicrobial; and
after exposing the reference sample to the antimicrobial, applying a spectroscopic/spectrometric technique to the reference sample to obtain reference spectrum data whose spectral profile has been influenced by exposing the sample to the antimicrobial.

Preferably, at least one of the reference microorganisms is of known susceptibility to the antimicrobial, and at least one of the reference microorganisms is of known resistance to the antimicrobial. In this way, the reference spectrum data obtained from the reference samples can be used (directly or indirectly) to inform whether a change in the spectral profile of spectrum data (obtained from a sample including the microorganism of interest) is indicative of susceptibility/resistance of the microorganism of interest to the antimicrobial.

The reference spectrum data obtained from the reference samples may be subsequently used (directly or indirectly) in a method of analysing a sample including the microorganism of interest according to the first aspect of the invention. As would be appreciated by a skilled person, there are a variety of ways in which this could be achieved, some of which will now be discussed.

In some examples, the reference spectrum data obtained from the reference samples could be included in a database containing reference spectrum data, which could e.g. be used by an algorithm configured to provide information regarding the susceptibility/resistance of the microorganism of interest to the antimicrobial directly from the spectrum data, e.g. described above in relation to the first aspect of the invention.

In some examples, the reference spectrum data obtained from the reference samples could be used to produce a look up table configured to transpose spectrum data to provide information regarding the susceptibility/resistance of the microorganism of interest to the antimicrobial, e.g. as described above in relation to the first aspect of the invention.

In some examples, the method according to the second aspect of the present invention may include, for each reference sample, using multiple data points within the reference spectrum data obtained from the reference sample to obtain respective reference spectral profile data which represents the spectral profile of the reference spectrum data obtained from the reference sample.

If reference spectral profile data is obtained, the information regarding the susceptibility/resistance of the microorganism of interest to the antimicrobial may be obtained from spectral profile data that is represented on a cluster plot by comparing the spectral profile data on the cluster plot with the reference spectral profile data obtained from the reference samples (which may e.g. be plotted on the same cluster plot or on a separate cluster plot).

Preferably, the reference spectral profile data obtained from the reference samples is used as labelled training data to produce a model configured to be applied to spectral profile data (e.g. obtained from the sample including the microorganism of interest, as described in relation to the first aspect of the invention), to obtain information regarding the susceptibility/resistance of the microorganism of interest to the antimicrobial, e.g. as described in relation to the first aspect of the invention.

If the reference spectral profile data obtained from the reference samples is used as labelled training data, the reference spectral profile data obtained from each reference sample may be labelled based on the known susceptibility/resistance to the antimicrobial of the reference microorganism included in that reference sample.

For avoidance of any doubt, the pre-analysis method does not need to be performed in the same place as, at the same time as, by the same party as, or using the same equipment as the subsequent method of analysing a sample including the microorganism of interest according to the first aspect of the invention. For example, the pre-analysis method could be used to produce a model, as discussed above, with the subsequent method of analysing a sample including the microorganism of interest according to the first aspect of the invention being performed using that model at a much later time by a different party and using different equipment.

As would be appreciated by a skilled person, if the reference spectrum data obtained from the reference samples is subsequently used (directly or indirectly) in a method of analysing a sample including the microorganism of interest according to the first aspect of the invention, then the spectroscopic/spectrometric technique used in the method of analysing a sample including the microorganism of interest according to the first aspect of the invention preferably matches the spectroscopic/spectrometric technique used in the pre-analysis method (although different apparatuses could be used). Similarly, the conditions under which the spectroscopic/spectrometric technique is applied to the sample in the method of analysing a sample including the microorganism of interest according to the first aspect of the invention preferably match or are similar to the conditions under which the spectroscopic/spectrometric technique is applied to the reference samples in the pre-analysis method.

In the pre-analysis method referred to above, each reference microorganism is referred to as having biochemical properties which are related to those of the microorganism of interest. In general, the biochemical properties of each reference microorganism only need to be related to those of the microorganism of interest to the extent that the spectral profile of the reference spectrum data (obtained from the reference samples) and the spectral profile of the spectrum data (obtained from the sample including the microorganism of interest) are influenced by exposure to the antimicrobial in a manner that is adequately similar to allow the reference spectrum data to be used to obtain information regarding the susceptibility/resistance of the microorganism of interest to the antimicrobial to be obtained from the spectrum data. This might be achieved, for example, by using reference microorganisms that are different strains of the microorganism of interest, as is the case with the experimental work below (where some strains of *E. coli* were used as reference microorganisms to produce a model that was subsequently used to provide an indication of whether other strains of *E. coli* were susceptible or resistant to three different antibiotics). However, it is not a requirement to use reference microorganisms that are strains of the microorganism of interest, e.g. provided that the phenotypic shifts due to susceptibility/resistance are present in the reference spectrum data (obtained from the reference microorganisms) in the same way.

The present inventors believe it would be straightforward for a skilled person to determine appropriate reference microorganisms to use for a given microorganism of interest, e.g. by using reference microorganisms (to obtain reference spectrum data) that are likely to be involved in an infection caused by that microorganism of interest. For example for a UTI, suitable reference microorganisms may include, amongst other bacteria: *Escherichia coli, Klebsiella* species, other coliforms, *staphylococci, Enterococcus faecalis* and *Pseudomonas aeruginosa*[29].

A skilled person will also appreciate from the present disclosure that, in order for a method according to the first aspect of the invention to be performed with a given microorganism of interest and a given antimicrobial, it will usually be necessary for the spectral profile of spectrum data obtained in accordance with the method according to the first aspect of the invention to be influenced adequately differently depending on whether the given microorganism of interest is susceptible or resistant to the given antimicrobial, i.e. to an extent that will allow information regarding the susceptibility/resistance of the microorganism of interest to the antimicrobial to be obtained from the spectrum data. Similarly, it will also normally be necessary for reference microorganisms having the properties described above to be available in relation to the given microorganism of interest. The experimental work provided below shows clearly that a method according to the first aspect of the invention can be performed on an *E. coli* bacterium using a variety of antibiotics having a wide range of action mechanisms, with other *E. coli* bacteria being used as the reference microorganisms.

Without wishing to be bound by theory, the inventors believe that since the biochemical properties of *E. coli* bacteria are so close to those of other Enterobacteriaceae and other Gram-negative bacteria, and given that the mechanism of action of antibiotics is the same against different bacteria, there is strong evidence to indicate that a method according to the first aspect of the invention could be used with any bacterium belonging to the Enterobacteriaceae or indeed on any Gram-negative bacteria.

The experimental work provided below also demonstrates that a method according to the first aspect of the invention can be performed with other types of bacteria (i.e. not just Enterobacteriaceae or Gram-negative bacteria), e.g. Gram-positive bacteria. Again, without wishing to be bound by theory, the inventors believe that antibiotics will target the same molecules in the microorganism irrespective of its Gram stain type.

Moreover, without wishing to be bound by theory, the present inventors believe that the methods described herein are capable of detecting phenotypic change associated with antimicrobial susceptibility/resistance in a microorganism, in a manner that correlates with phenotypic testing as carried out measuring growth of that microorganism on culture plates. The present inventors therefore expect that the methods described herein will translate across a broad range of microorganisms in a similar manner to culture plate testing, or other in vitro methods used to determine susceptibility.

Since the experimental work described below was performed using a variety of antibiotics having a very wide range of action mechanisms, the present inventors believe that there is very strong evidence to indicate that a method according to the first aspect of the invention could be used with all types of antibiotics, not just the specific examples used in the experimental work, since, without wishing to be bound by theory, the phenotypic changes in the microorganisms are believed to be generic and reproducible as demonstrated in the accompanying experimental data.

The inventors also believe that a method according to the first aspect of the invention could be used with fungal microorganisms/antifungals, because, without wishing to be bound by theory, the phenotypic shift of the fungus is expected to be similar or the same and related to the mode of action of the antifungal agent.

The inventors also believe that a method according to the first aspect of the invention could be used with parasitic microorganisms/antiparasitics, because, without wishing to be bound by theory, again the phenotypic shift of the parasite is expected to be similar or the same and related to the mode of action of the antiparasitic agent.

The inventors also believe that a method according to the first aspect of the invention could be used with viruses/antivirals, because, without wishing to be bound by theory, the effect on the viral agent is expected to be manifest on a host organism on which the virus is cultured. In this case the reporter phenotype would not be the virus per se but it would be the phenotypic response elicited by the virus now interacting differently with the cell that is supporting its growth. Without wishing to be bound by theory, the inventors believe this would cause a reproducible shift in the UV-vis spectrum that can be correlated to resistance or sensitivity to the antiviral.

Naturally, and as a skilled person would readily appreciate, some routine changes to the methodology described in the experimental work section below would be appropriate if using a method according to the first aspect of the invention with microorganisms different to those exemplified.

For example, if using a method according to the first aspect of the invention with a viral microorganism of interest, the sample would typically include a host organism on which the viral microorganism of interest is cultured. In this case, as indicated above, the spectral profile of the spectrum data would (it is believed) be influenced by a phenotypic response in the host organism elicited by exposing the virus to the antiviral, i.e. so that information regarding the susceptibility/resistance of the viral microorganism of interest to the antiviral would be obtained indirectly through a phenotypic response in the host organism.

A third aspect of the invention may provide an apparatus suitable for performing a method according to the first aspect and/or second aspect of the invention.

The third aspect of the invention may therefore provide:

An apparatus for analysing a sample including a microorganism of interest, the apparatus including:

a spectroscopic device configured to apply a spectroscopic/spectrometric technique to a sample that has been exposed to an antimicrobial to obtain spectrum data whose spectral profile has been influenced by exposing the sample to the antimicrobial; and a processing unit configured to obtain information regarding the susceptibility/resistance of the microorganism of interest to the antimicrobial from the spectrum data.

The apparatus may be configured to implement, or have means for implementing, any method step described in connection with any above aspect of the invention.

The apparatus may include a model, database and/or a "look up" table as discussed above.

A fourth aspect of the invention may provide a computer-readable medium having computer-executable instructions configured to cause a computer to perform the data analysis steps associated with a method according to the first aspect and/or second aspect of the invention.

For example, the fourth aspect of the invention may provide:

A computer-readable medium having computer-executable instructions configured to cause a computer to perform a method of analysing spectrum data, wherein the spectrum data has been obtained by applying a spectroscopic/spectrometric technique to a sample including a microorganism of interest after the sample has been exposed to an antimicrobial such that the spectrum data has been influenced by exposing the sample to the antimicrobial, wherein the method includes:

obtaining information regarding the susceptibility/resistance of the microorganism of interest to the antimicrobial from the spectrum data.

The method may include any data processing method steps described in or associated with the first aspect and/or second aspect of the invention.

The computer-readable medium may also have computer-executable instructions configured to control a spectroscopic device to apply a spectroscopic technique to a sample that has been exposed to an antimicrobial to obtain spectrum data whose spectral profile has been influenced by exposing the sample to the antimicrobial.

The computer-readable medium may include a model, database and/or a "look up" table as discussed above.

A fifth aspect of the invention may provide a computer-readable medium storing a database as discussed above.

For example, the database may contain reference spectrum data, e.g. obtained by exposing samples containing reference microorganisms of known susceptibility/resistance to the antimicrobial.

The database may include reference spectrum data obtained as described above with reference to the second aspect of the invention, for example.

The invention also includes any combination of the aspects and preferred features described except where such a combination is clearly impermissible or expressly avoided.

BRIEF DESCRIPTION OF THE DRAWINGS

Examples of our proposals are discussed below, with reference to the accompanying drawings in which.

DETAILED DESCRIPTION

Figure 1:
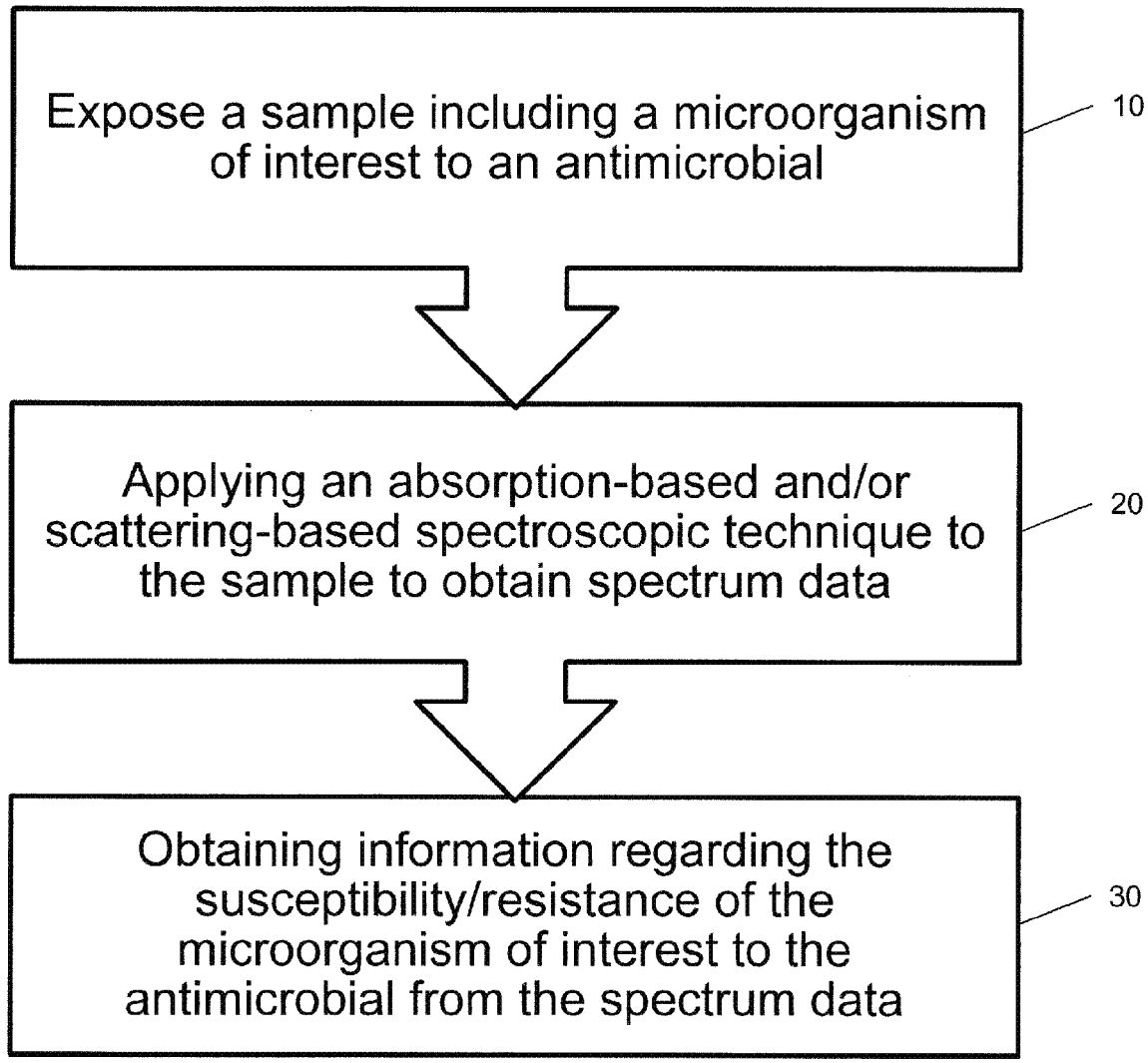
FIG. 1 shows a method of analysing a sample including a microorganism of interest

FIG. 1 shows an example method of analysing a sample including a microorganism of interest, which may include:
 exposing the sample to an antimicrobial (10);
 after exposing the sample to the antimicrobial, applying an absorption-based and/or scattering-based spectroscopic technique (e.g. using the spectroscopic device 110, see below) to the sample to obtain spectrum data (20) whose spectral profile has been influenced by exposing the sample to the antimicrobial;
 obtaining information regarding the susceptibility/resistance of the microorganism of interest to the antimicrobial from the spectrum data (30).

In some embodiments, the step of obtaining information (30) may include:
 using multiple data points within the spectrum data to obtain spectral profile data which represents the spectral profile of the spectrum data; and obtaining information regarding the susceptibility/resistance of the microorganism of interest to the antimicrobial from the spectral profile data.

By way of example, the sample may contain a UTI-causing bacterium, e.g. as obtained by a clinician in a medical environment.

Preferably, applying the absorption-based and/or scattering-based spectroscopy technique to the sample includes irradiating the sample with UV-Vis and/or IR radiation. In some embodiments, UV-Vis radiation is preferred.

The spectral profile data may be obtained according to an unsupervised statistical technique such as PCA, with the multiple data points within the (post-exposure) spectrum data being used as inputs for the statistical technique.

In the experimental work described below, PCA was used on multiple data points within spectrum data to obtain spectral profile data which represents the spectral profile of the spectrum data.

The information regarding the susceptibility/resistance of the microorganism of interest to the antimicrobial from the spectral profile data may be obtained by applying a supervised model (such as DFA or PLS-DA) to the spectral profile data, where the supervised model has been produced using labelled training data. The labelled training data may be reference spectral profile data obtained as described above with reference to the second aspect of the invention, for example.

In the experimental work described below, PC-DFA and PLS-DA, were used to explore the relationship between the FT-IR or UV-Vis spectra and the different types of antibiotics individually and in combination.

In the experimental work described below, the results of PC-DFA are shown as cluster plots; these allow one to visualise the changes in the spectral profiles before and after antimicrobial exposure of the microorganisms analysed. By contrast, the results of PLS-DA are tabulated and these show objective classifications according to whether the microorganisms of interest are sensitive or resistant to the antimicrobial used.

Figure 2:
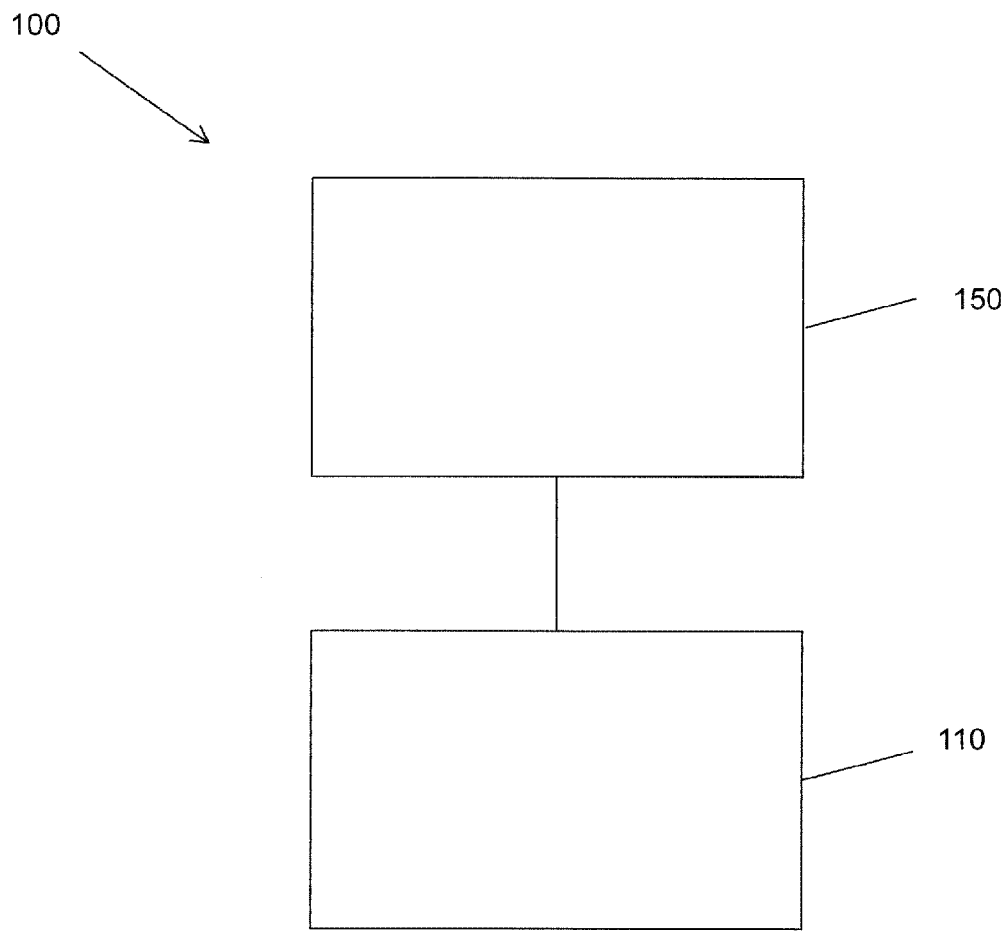
FIG. 2 is a schematic diagram showing an apparatus for performing a method of analysing a sample including a microorganism of interest.

FIG. 2 shows an apparatus 100 for performing a method of analysing a sample including a microorganism of interest. The apparatus 100 may, for example, be used in a clinical environment to obtain information regarding the susceptibility/resistance of a bacterium of interest to an antibiotic.

The apparatus 100 includes a spectroscopic/spectrometric device 110 and a processing unit 150.

Preferably, the spectroscopic/spectrometric device 110 is for applying a spectroscopic/spectrometric technique, more preferably an absorption-based and/or scattering-based spectroscopic technique, to a sample including a microorganism of interest, after the sample has been exposed to an antimicrobial, to obtain spectrum data whose spectral profile has been influenced by exposing the sample to the antimicrobial, e.g. as described above.

Preferably, the spectroscopic/spectrometric device 110 is an ultraviolet-visible ("UV-Vis") spectrometer for applying an UV-Vis spectroscopic technique to the sample or a FT-IR spectrometer for applying a FT-IR spectroscopic technique to the sample.

The processing unit 150 may be a general purpose computer, for example, and is preferably configured to use multiple data points within the spectrum data to: obtain spectral profile data which represents the spectral profile of the spectrum data; and obtain information regarding the susceptibility/resistance of the microorganism of interest to the antimicrobial from the spectral profile data (e.g. by applying a model to the spectral profile).

For an integrated system the spectroscopic device 110 and the processing unit 150 could be integrated into a single system.

EXPERIMENTAL WORK

This section describes experimental work that has been carried out in relation to this invention.

Experimental Work 1

In this experimental work, FT-IR spectroscopy with data processing was used to identify phenotypic changes in many strains (>200) of E. coli after exposure to different antibiotics. Additionally, UV-Vis spectroscopy was used to show that UV-Vis is also capable of measuring separation between E. coli bacterial samples on a cluster plot, according to whether those bacterial samples are resistant or not, even after only 10 min from exposure of the bacteria to the antibiotic.

A preferred aim of this experimental work was to investigate the ability of both UV-Vis and FT-IR used together with chemometric data processing in identifying common uropathogenic bacteria such as E. coli from pure cultures and clinical samples. Another aim of this experimental work was to employ FT-IR spectroscopy in combination with chemometric data processing to investigate changes in the phenotype of uropathogenic E. coli (UPEC) strains to antibiotics, thus potentially identifying their degree of sensitivity to the antibiotics.

In this work, E. coli K12 bacteria were grown in pure cultures. At the start of the exponential bacterial growth phase, one of three antibiotics (amikacin, ampicillin or trimethoprim) or a combination of these antibiotics at known quantities, were added to the bacterial cultures. Samples were collected 75 min after addition of the antibiotic(s) and analysed using FT-IR. Multivariate analyses, including PLS-DA, were then used to analyse the data and predict antimicrobial susceptibility levels. PLS-DA accuracy predictions for the various models acquired were very good with model accuracies ranging between 86 and 100%. These results indicate that clear separation among UPEC can be achieved based on their response to different types of antibiotics within 75 min after exposure to the antibiotic(s). The ability of FT-IR spectroscopy for use in rapid and accurate antibiotic resistant profiling of UTI causing bacteria is therefore clearly demonstrated.

Experimental Work 1

Material and Methods

Bacteria

The E. coli K12 MG1655 strain used was obtained from Simon Andrews (Reading University, UK). E. coli K12 cultures were stored at −80° C. before use. After thawing, bacterial cultures were sub-cultured three times in nutrient agar (Oxoid Hampshire, UK), at 37° C. for 18-20 h prior to use in the experiments.

Minimum Inhibitory Concentration (MIC)

The E. coli K12 MIC for amikacin, ampicillin and trimethoprim were estimated using a bioscreen spectrophotometer at 600 nm and after 24 h of incubation at 37° C. A range of different concentrations of antibiotic were used to establish the MIC employing a standardised method[17].

Growth Curve

At the beginning of each experiment, a single colony of E. coli K12 was grown in 50 mL of nutrient broth at 37° C. for 24 h in a shaking incubator at 200 rpm. 50 μL of nutrient broth containing the bacteria were then retrieved and inoculated in 50 mL of nutrient broth, which were incubated again at 37° C. in a shaking incubator at 200 rpm. The latter was sampled at 30 min intervals for 12 h and the optical density was measured at 600 nm in order to prepare growth curves and define the start of the exponential growth phase. This was the time point chosen for addition of the antibiotic(s).

Sample Preparation

E. coli K12 was grown in 50 mL of nutrient broth at 37° C. for 150 min until it reached the start of the exponential phase. One of the three different antibiotics or different combinations of these antibiotics were then added to the bacterial cultures. The different percentages of the MIC tested for single antibiotic were at 50%, 100% and 400% of the MIC. Similarly, in the antibiotic combination mixtures, each combination pair used was tested at 50%, 100% or 400% of the MIC for each antibiotic used. Preliminary experimentation of sampling at different time points after addition of the antibiotic(s) indicated that adequate differentiation was seen after 75 min. During the formal experiments, sampling was therefore undertaken 75 min after antibiotic addition and analysed using the FT-IR. Ten biological replicates were collected for each antibiotic concentration.

UV-Vis Spectroscopy

UV-Vis analysis in transmission mode was performed using a Thermo Biomate 5 UV-Vis spectrometer. A medium blank was used as the reference material. Samples were presented directly in liquid form within cuvettes to the instrument; note this is in contrast to FT-IR where samples were dried prior to analysis (as is generally required for good results from FT-IR spectroscopy). All analyses were performed manually. The spectral range used was 300 nm to 800 nm. Each spectrum acquisition lasted a few seconds and a total of 96 spectra were collected.

FT-IR Spectroscopy

FT-IR analysis in transmission mode was performed using a Bruker Equinox 55 infrared spectrometer carrying a deuterated triglycine sulfate (DTGS) detector (Bruker Ltd, Coventry, UK) employing a motorised microplate module HTS-XT™. Sample mixing was undertaken using a rotational mixer for 30 s. 20 μL from each sample were then pipetted onto a ZnSe sample carrier/plate (which can hold 96 samples), and oven dried at 40° C. for 25 min. In total 3 replicates were taken from each sample and each replicate was placed at a random spot across the ZnSe plate[18]. The wavenumber range collected was 4000 to 600 $cm^{-1}$, with a resolution of 4 $cm^{-1}$, and 64 scans were co-added and averaged. Each spectrum acquisition lasted 60 s and a total of 630 spectra were collected.

Pre-Processing

Matlab ver. 7 (The Mathworks, Inc Matick, Mass.) was used to pre-process the ASCII data exported from FT-IR and UV-Vis, and scaling of the FT-IR data set was performed using the extended multiplicative scatter correction (EMSC)[19]. EMSC is a normalisation technique that removes the natural light scattering effect caused predominantly by small particles compared to larger particles registered in the spectra, allowing for the detection of mainly the actual light absorbance by sample molecules.

For UV-Vis the data were analysed directly and not pre-processed.

Multivariate statistical techniques such as cluster analysis and supervised discriminant-based techniques, PC-DFA and PLS-DA, were subsequently used to explore the relationship between the FT-IR or UV-Vis spectra and the different types of antibiotics individually and in combination.

Data Analysis—Principal Component Discriminant Function Analysis (PC-DFA)

A first stage of data analysis involved the use of principal component analysis (PCA). PCA is an unsupervised technique, which does not use any prior information from the experiments in order to construct a model. Its aim is to simplify spectral data from a high number of variables into a smaller number of indices (each called a "principal component" or "PC"), simultaneously retaining the original data variance by identifying data patterns. This is achieved as each PC becomes a representation of a group of data with a linear relationship, at the same time being completely uncorrelated to the subsequent PC which corresponds to a different data dimension. PCs are arranged in a descending order in terms of the degree of original data variance they represent with the first PC representing the greatest amount of original data variance. Addition of all the PCs thus yields the entire original data variance, with the first 5 PCs nearly always corresponding to almost 95% of that variance[11,20-22].

In a second stage, discriminant function analysis (DFA), a supervised technique, was used. This chemometrics technique forms a model by taking into account the structure of data collected from the experiment, thus having a priori experimental knowledge. Using this knowledge it then discriminates data into groups (bacterial classes of treatment) based on the PCs obtained from the PCA in an attempt to reduce intra-group variance and widen inter-group variance[23].

In order to minimize bias and establish statistical validity of a model in multivariate data analysis, validation of supervised learning algorithms, which can be significantly influenced by the initial data, is required. Different approaches can be employed. These mainly use re-sampling of the initial data and testing of the model. Validation of the PC-DFA model for the FT-IR data was therefore performed. Data were divided into a training set consisting of the first seven biological replicates (seven groups for each antibiotic or combination of antibiotic), which were used to construct a PC-DFA model, and a test set consisting of the remaining three biological replicates. The PC-DFA model construction was followed by test set data projection into the PCA space and further projection of the resultant PCs onto the PC-DFA space[24]. Coincident projection of both the test and training data in the DFA space was indicative of model validity.

For analysis of the UV-Vis data (see FIG. 9), the groups used were the different samples and times. 32 groups were used and these were from 2 resistant and 2 sensitive microorganisms (4 different E. coli bacteria in total). These bacteria were exposed to either the antimicrobial (ampicillin) or blank water (i.e., no exposure to the antimicrobial) and were sampled after 10 min, 20 min, 30 min and 75 min exposure.

Data Analysis—Partial Least Squares Discriminant Analysis (PLS-DA)

PLS-DA is a classical regression technique. As it is dealing with a number of classes rather than a single class, it employs a partial least squares 2 (PLS2) algorithm which attempts to increase separation between classes by calculating a representative Y value for each dependent variable within the class, assigning a class vector value between 0 and 1. A predicted value closest to 1 indicates how close the variable is in belonging to the class, thus a value of 1 indicates absolute "fitness" while a value of 0 shows no "fitness" into the class[25,26]. The maximum or minimum Y value at which a variable can be assigned to the class can be set higher or lower along the 0 to 1 scale, in that way adjusting the model's sensitivity and specificity parameters.

In order to obtain unbiased estimates, model validation for PLS-DA needs to be performed. Such validation is performed parallel to modelling using bootstrapping analysis[27,28]. Bootstrapping is a type of random resampling approach and in this case the N samples collected were analysed using a process of random selection of individual samples from the group X times, each time recording and then replacing the sample back to the main sample group. All selected samples finally form the training set. As during this process each sample can be selected more than once or not at all, the training set normally contains about 63.2% of the whole number of samples. These are used for modelling while the remaining 36.8% of samples are used as a test group to check precision, accuracy and validation. The whole process was performed 1000 times and the final model was obtained from the average values from the test data sets.

Experimental Work 1

Results and Discussion

Minimum Inhibitory Concentration (MIC)

After 24 h of incubation at 37° C. using a bioscreen spectrophotometer at 600 nm the *E. coli* K12 MIC was found to be 300 μg/mL for the trimethoprim and 10 μg/mL for both the amikacin and ampicillin.

Growth Curve

A sample of *E. coli* K12 (a laboratory strain, see above) was grown from pure culture until the start of the exponential growth phase (clear start of growth). An antibiotic (ampicillin) at the minimum inhibitory concentration (MIC) was added to the sample at the start of the exponential growth phase, thus eliciting a phenotypic response, and then the cells cultured in the presence of the antibiotic.

Figure 3:
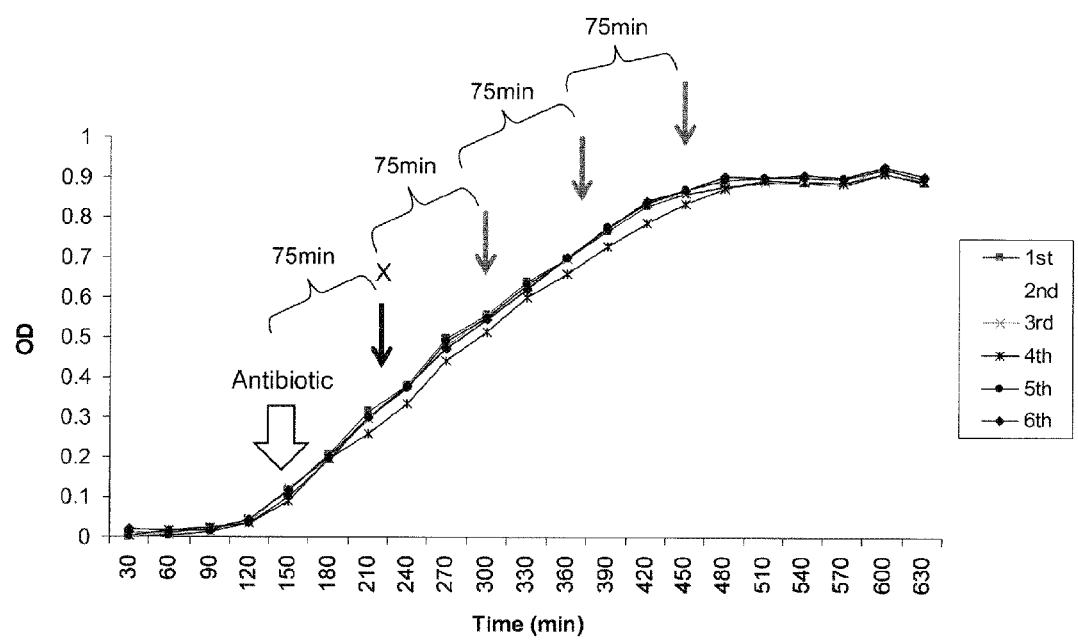
FIG. 3 is a graph showing six growth curves based on optical density for *E. coli* K12 when an antibiotic was added at the start of the exponential growth phase.

This experiment was repeated six times in order to establish the pattern of growth of the bacterium against time as seen in FIG. 3.

The growth curves shown in FIG. 3 appear to be consistent with the expected bacterial growth curve.

These preliminary experiments were repeated a number of times, with various concentrations/mixtures of three different antibiotics (amikacin, ampicillin, trimethoprim) being added at the start of the exponential growth phase, which was at ~150 min, as illustrated by arrow in FIG. 3, and then samples were taken at 75 min intervals as illustrated by the remaining arrows in FIG. 3 to assess the effect on growth using FT-IR and chemometrics.

As very promising results were obtained during the first 75 min period (arrow labelled "X") this was the time period used for most of the antibiotic exposure experiments described below.

Subsequent experimental work (described below) has shown that promising results can be obtained at time periods significantly less than 75 minutes after initial exposure of the sample to an antibiotic.

Single and Combination Antibiotic Testing at 75 Min Intervals

The results from the PC-DFA for the single antibiotic testing when samples were taken at each of the 75 min intervals indicated good separation between the three antibiotics (data not shown). This result showed that the trimethoprim, ampicillin and amikacin appear at different directions and areas on the PC-DFA panel with the greatest movement between time points in the PC-DFA space occurring between the 0 min time point and the 75 min time point. The results from the PC-DFA for the antibiotic combinations showed separation into four different groups and each group followed a different direction on the PC-DFA panel (data not shown). The presence of some antibiotics appeared to influence the direction of separation of the binary antibiotic groups more strongly than others. For example, trimethoprim, trimethoprim with ampicillin and trimethoprim with amikacin appeared in one area, amikacin with ampicillin and ampicillin appeared together in the same area, while amikacin alone appeared in a different direction compared with the previous groups.

As clear differences were obtained after 75 min of incubation in the presence of the antibiotic(s), this time point was used for most of the experimental work described below, though later experimental work has shown that useful results can be obtained with an even smaller time gap after exposure to an antimicrobial.

Single Antibiotic Testing

Figure 4:
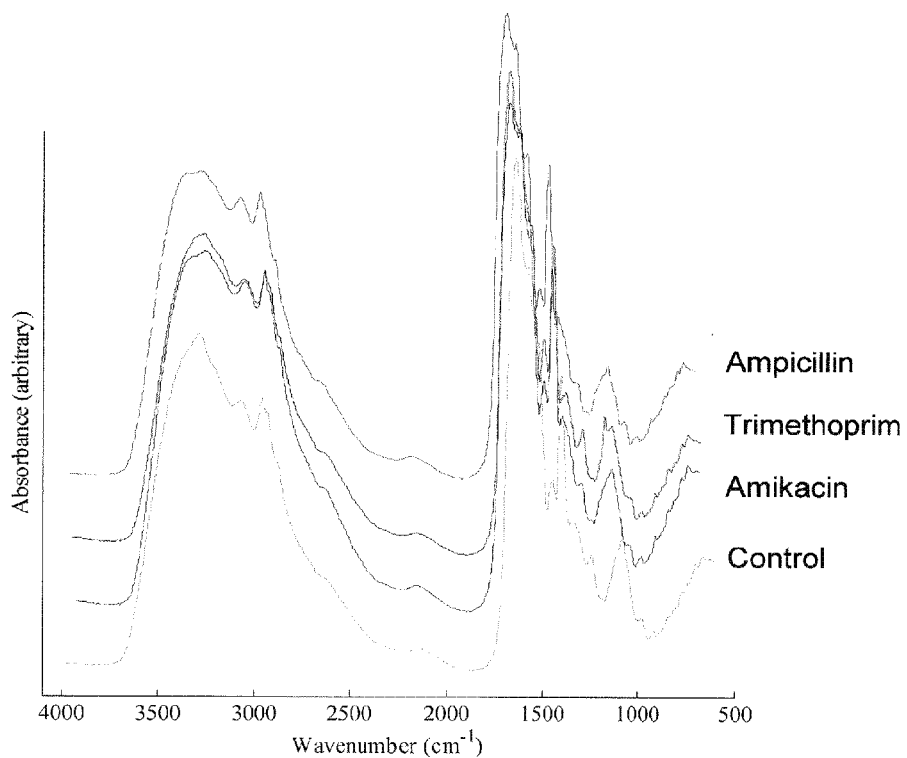
FIG. 4 shows typical FT-IR spectra collected from *E. coli* K12 exposed to each of three antibiotics at 100% minimum inhibitory concentration (MIC) for 75 min. A control with no antibiotic addition is also shown.

Representative spectra collected from the FT-IR are shown in FIG. 4.

Even though some differences can be distinguished between each single antibiotic and the control in FIG. 4, these fingerprints appear to be visually very similar. For this reason cluster analysis was employed in order to try and analyse the data further in order to reveal any potential differences.

The Principal Component-Discriminant Function Analysis (PC-DFA) approach was used as a discriminator between the spectra from the three different antibiotics.

Figure 5:
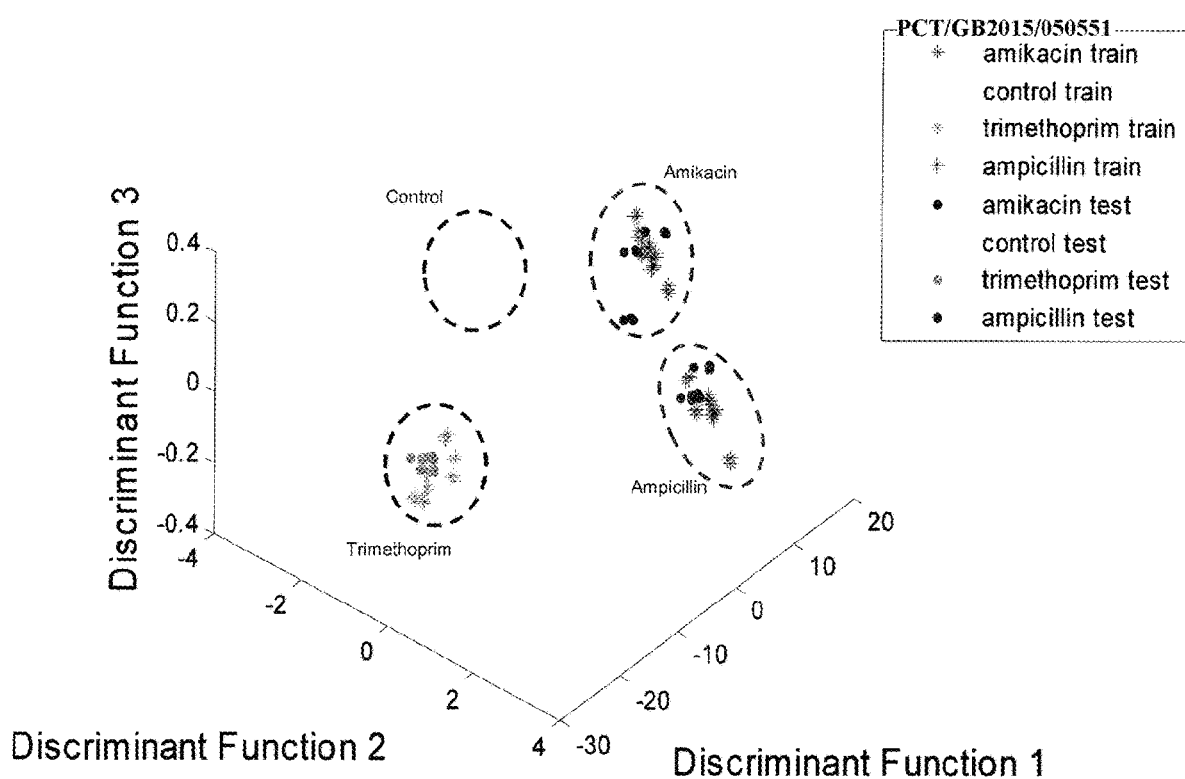
FIG. 5 shows the results of cluster analysis using principal components-discriminant function analysis (PC-DFA) constructed from FT-IR spectra from the *E. coli* K12 bacteria when exposed to pure antibiotic at 100% MIC.

FIG. 5 illustrates this separation when the 100% antibiotic MIC is used for each of three different antibiotics (amikacin, ampicillin, trimethoprim) and a control.

The DFA algorithm used PCs 1-8, which accounted for 99.32% of the total variance.

In FIG. 5, the different shades represent the three different antibiotics, and the control (bacteria grown in broth for 75 min without antibiotic addition). The star symbols represent the train data and the circles represent the test data which are used to validate the model. The fact that the test data are close to the training data supports the analysis.

Ten separate biological replicates were obtained to collect these data for each group. All PC-DFA plots were validated. In this process the 10 repeats were split into two groups: the training set (star shapes on graph) contained repeats 1-7 and the test set (circle shapes) repeats 8-10. If the test set is located closely with the training set then the clustering is valid. In all cluster plots this was found to be the case highlighting the excellent reproducibility of the study, and therefore that the phenotypic response to the antibiotic was consistent.

In FIG. 5 there is also very clear separation between the different types of antibiotics making it easy to distinguish which antibiotic has been used even though exposure had only been for 75 min. For 50% and 400% antibiotic MICs a generally similar trend was observed (figures not shown).

Partial least squares discriminant analysis (PLS-DA) was then used to create a prediction model for the type of antibiotic used. In order to check the predictive accuracy of the model bootstrapping was used where the algorithm (model) created subsequently run up to 1000 different combinations of test and training sets based on the collected data. The results from this analysis when 100% antibiotic MIC is used are shown in Table 1, below.

TABLE 1

A confusion matrix of partial least squares-discriminant analysis (PLS-DA) predictions for bacteria exposed to various antibiotics at 100% MIC.

| Actual Group | Predicted Group | | | |
| --- | --- | --- | --- | --- |
| | Amikacin | Ampicillin | Trimethoprim | Control |
| Amikacin | 98.43% | 1.57% | 0% | 0% |
| Ampicillin | 0% | 100% | 0% | 0% |
| Trimethoprim | 0% | 0% | 100% | 0% |
| Control | 0% | 0% | 0% | 100% |
| Overall accuracy: 99.61% | | | | |

As can be seen from Table 1, the predicted group column shows the accuracy of the model in predicting the correct group containing an antibiotic, or control. The overall (i.e. average) accuracy of this model was 99.61% which is excellent.

The overall accuracy for the other two antibiotic concentrations, 50% of MIC and 400% of MIC (corresponding tables not shown) were 99.87% and 99.98% respectively, as shown in Table 2, below.

TABLE 2

A summary of the PLS-DA overall prediction accuracy for the three antibiotics tested at various MICs to $E.\ coli$ K12.

| Percentage (%) of MIC | Pure antibiotics |
| --- | --- |
| 50% | 99.87% |
| 100% | 99.61% |
| 400% | 99.98% |

Interim Discussion

The experimental work discussed so far shows that FT-IR spectroscopy, in combination with multivariate statistical methods such as PC-DFA and PLS-DA, was able to identify significant phenotypic changes among the $E.\ coli$ K12 bacterial cells when exposed to different antibiotics. The predictive accuracy of all models for the single antibiotic agents at 99% appears to be excellent and very encouraging.

Results from antimicrobials having the form of binary antibiotic mixtures (data not shown) were also positive despite a lower predictive accuracy of 85%.

Overall, the use of FT-IR spectroscopy in combination with chemometric analysis in rapidly profiling pathogenic bacteria based on their response to different antibiotics has been shown to be very pragmatic and attainable.

Determining Susceptibility/Resistance

Figure 6:
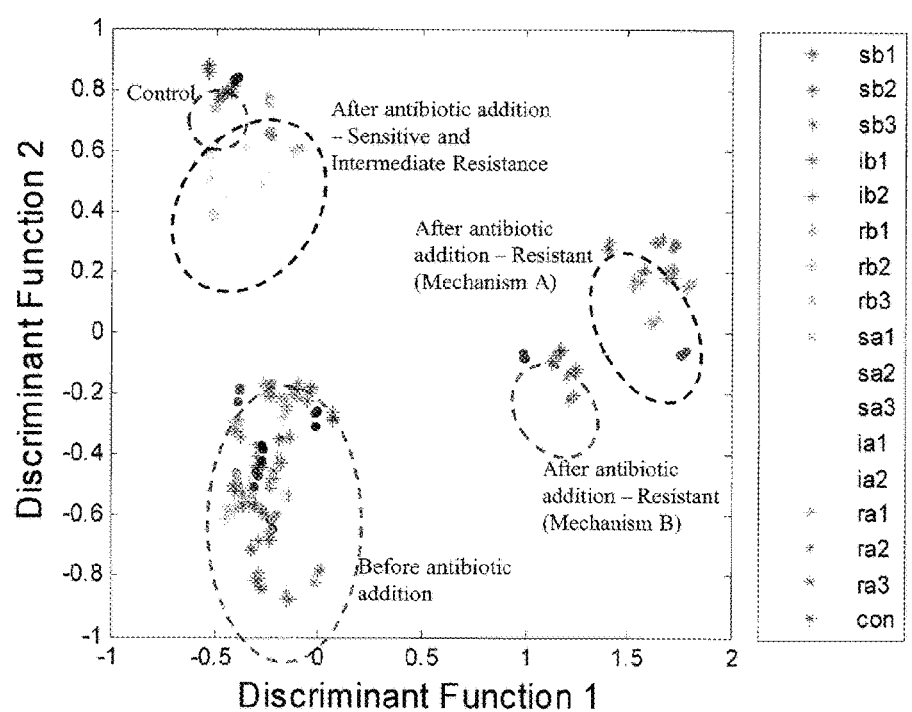
FIG. 6 shows the results of PC-DFA cluster analysis showing the effects on bacterial phenotype from eight clinical *E. coli* strains that have different levels of antibiotic resistance.

In FIG. 6, the $E.\ coli$ strains used had different levels of susceptibility to the antimicrobial ampicllin:
  sensitive (3 bacteria labelled s[a/b]1, s[a/b]2, s[a/b]3 (where b was used for before and a for after ampicillin exposure)
  intermediate resistance (2 bacteria labelled i[a/b]1, i[a/b]2 (coding as above)) or
  fully resistant (3 bacteria labelled r[a/b]1, r[a/b]2, r[a/b]3 (coding as above))

Note that in FIG. 6, the resistant bacteria have a different trajectory compared to the sensitive and intermediate resistance isolates.

The results shown in FIG. 6 therefore demonstrate that FT-IR can be used to differentiate microorganisms that are either (a) sensitive, (b) resistant, or (c) have intermediate resistance to an antimicrobial. Note that all bacteria cluster together before antimicrobial exposure but are located in different places in the plot and 3 clusters are seen: (i) the sensitive and intermediate resistance after antimicrobial exposure; (ii) 2 resistant bacteria with mode of resistance A; (iii) 1 resistant bacterium with mode of resistance B.

This was a significant finding and it was therefore of interest to test whether the technique could cluster microorganisms based on their differing modes of resistance after they had been exposed to the antimicrobial to which they are resistant.

Determining Mechanism of Resistance

Five different $E.\ coli$ bacteria were analysed that had been selected because they were resistant to ampicillin and were resistant in one of three different ways.

Bacteria r1 and r4 shared one particular resistance mechanism, bacteria r2 and r5 shared a different resistance mechanism, while bacterium r3 possessed a third mode of resistance that was different from all of the other bacteria.

Again these five bacteria were sampled and measured using FT-IR before exposure to the antimicrobial ampicillin and 75 min after.

Figure 7:
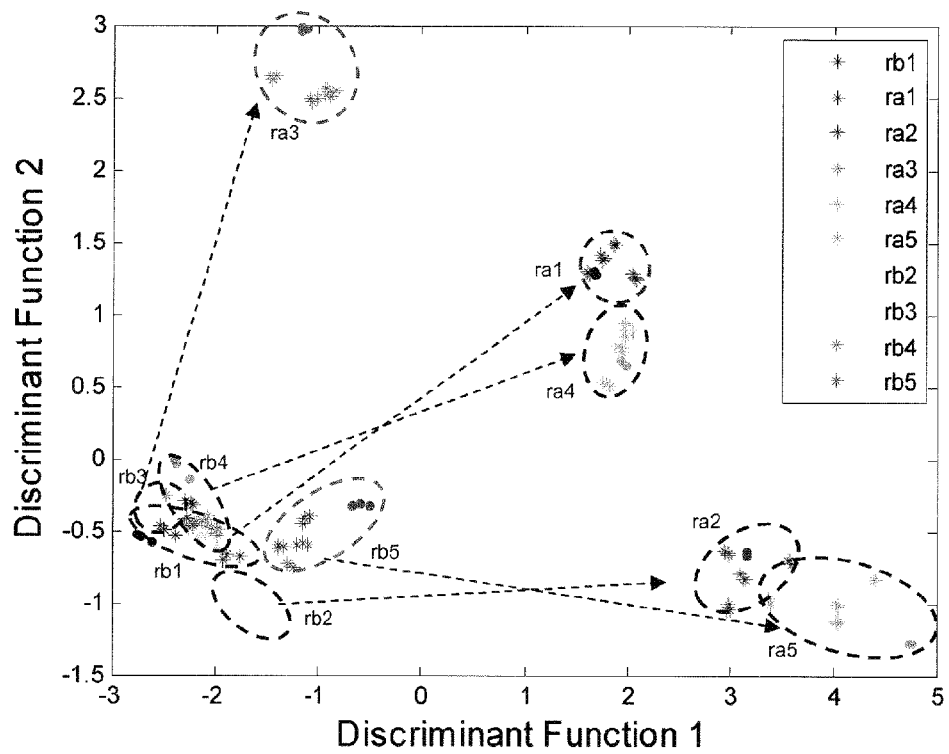
FIG. 7 shows the results of PC-DFA cluster analysis showing the effects on bacterial phenotype of 75 min exposure to ampicillin for five different *E. coli* which are all ampicillin resistant bacteria, but have different modes of resistance to ampicillin.

The differentiation that is seen in FIG. 7 results in three different clusters which are based on different antibiotic resistant mechanisms.

The results shown in FIG. 7 therefore demonstrate that FT-IR is capable of classify bacteria based on their different resistance mechanisms to the same antimicrobial.

Clinical Isolate Study 200 different clinical $E.\ coli$ isolates that are either sensitive or resistant to one of three different antibiotics were analysed with FT-IR before and after exposure to the antimicrobial.

The three different antimicrobials used were ampicillin, trimethoprim, ciprofloxacin. These antimicrobials are commonly used to treat UTIs, for example.

Following this a series of PLS-DA models were constructed to attempt to predict whether the bacteria was resistant or sensitive. These real values were known by classical microbiology and were used as the predictors (Y value). Bootstrap validation was used and 1000 re-samplings were made. The PLS-DA models included trying to predict the resistance or sensitivity before addition of the antibiotic (Table 3: first 3 rows) as well as trying to predict the resistance or sensitivity after addition of the ampicillin, trimethoprim, or ciprofloxacin (Table 3: last 3 rows).

In addition to bootstrap validation we also generated null models where the Y value (resistance or sensitivity) were randomised (also referred to as permuted) (Table 4). If there was no bias these predictions should be close to 50%.

TABLE 3

PLS-DA prediction accuracy for 200 different clinical isolates that are either sensitive or resistant to one of three different antibiotics (values in parentheses are the clinical-relevant doses used): ampicillin (16 mg/L), trimethoprim (32 mg/L), ciprofloxacin (4 mg/L), with FT-IR spectroscopy being performed 75 min after initial exposure to the antibiotic.

| Antibiotic | Accuracy for Resistant Isolates | Accuracy for Sensitive isolates | Overall model accuracy |
| --- | --- | --- | --- |
| | Before antibiotic addition | | |
| Ampicillin | 54.36% | 53.33% | 53.84% |
| Trimethoprim | 49.07% | 52.57% | 50.82% |
| Ciprofloxacin | 57.76% | 51.76% | 54.76% |
| | After antibiotic addition | | |
| Ampicillin | 87.80% | 90.53% | 89.16% |
| Trimethoprim | 84.24% | 80.26% | 82.25% |
| Ciprofloxacin | 91.16% | 65.68% | 78.42% |

TABLE 4

PLS-DA prediction accuracy for the same data shown in Table 3, except for the predictions being randomly permuted such that a random null distribution is seen. This values should indeed be around 50% and highlights that the models above are real.

| Antibiotic | Accuracy for Resistant Isolates | Accuracy for Sensitive isolates | Overall model accuracy |
|---|---|---|---|
| Before antibiotic addition | | | |
| Ampicillin | 49.01% | 51.00% | 50.01% |
| Trimethoprim | 49.50% | 51.79% | 50.65% |
| Ciprofloxacin | 45.82% | 51.86% | 48.84% |
| After antibiotic addition | | | |
| Ampicillin | 48.90% | 49.15% | 49.02% |
| Trimethoprim | 48.94% | 50.63% | 49.78% |
| Ciprofloxacin | 43.37% | 52.14% | 47.75% |

It is clear from Tables 3 and 4, that antibiotic addition is needed to achieve a correct classification.

Time Course Trajectory

The ability of FT-IR and chemometrics to distinguish changes in samples containing sensitive or resistant bacteria before and after addition of antibiotic earlier than the 75 min period was tested. One ampicillin sensitive and one ampicillin resistant UTI pathogen were separately investigated and sampled during regular time intervals from time 0 min (antibiotic added) to 75 min (i.e. at 0, 10, 20, 30, 40, 50, 60 and 75 min).

Figure 8:
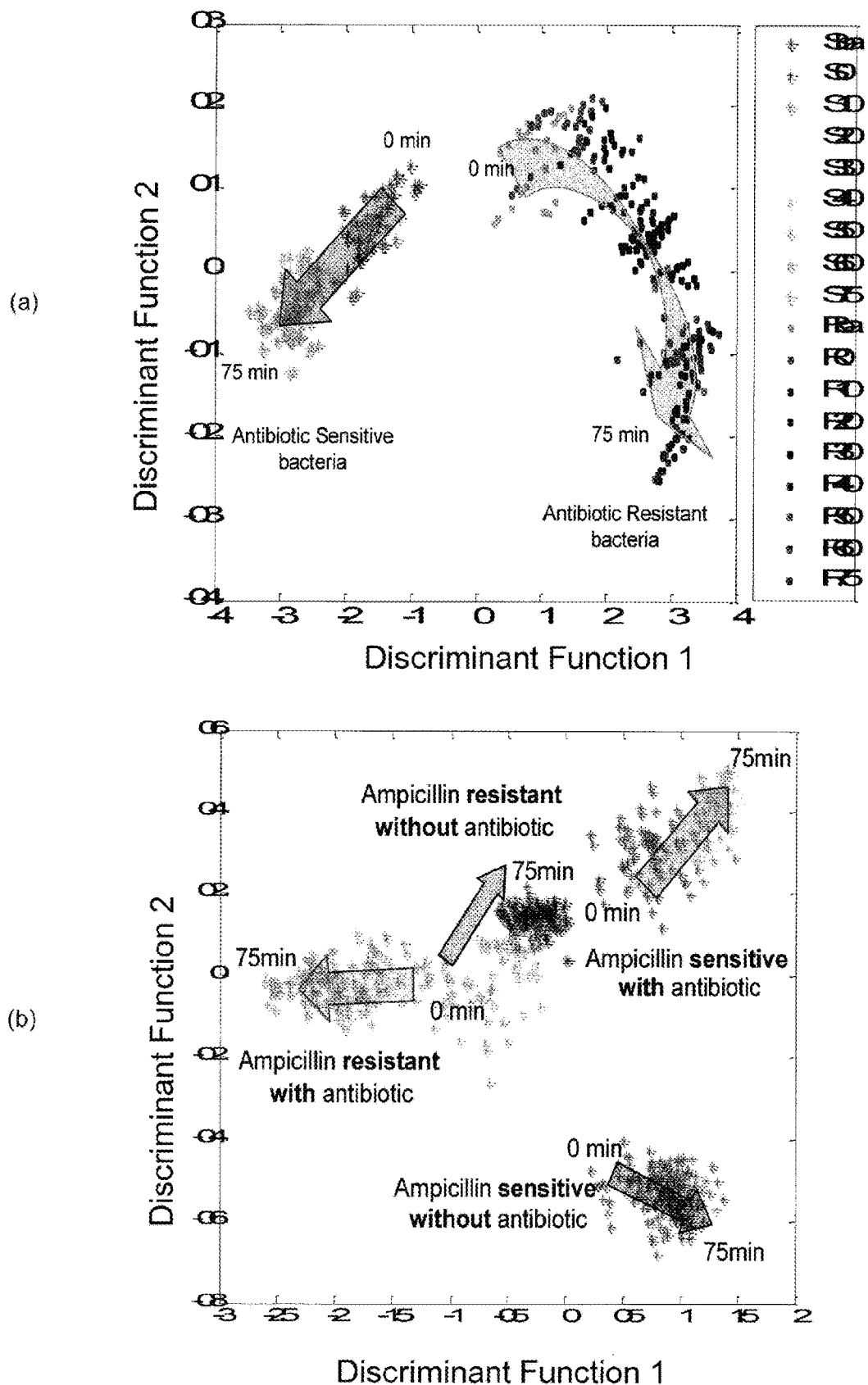
FIG. 8 shows Cluster plots showing the phenotypic effects on antibiotic sensitive and resistant bacterial samples obtained from FT-IR (a) during the initial 75 min period after the addition of the ampicillin antibiotic and (b) comparison of data between bacteria with and without ampicillin addition.

The data were analysed again using PC-DFA and FIG. 8 demonstrate a clear time course trajectory and that the phenotypic effect occurs well before 75 min.

Prediction Accuracy

The next step of the analysis involved PLS-DA cross validation for each time point tested, in order to obtain the models' accuracy and ascertain whether it would be feasible to accurately predict bacterial antibiotic sensitivity at one of these earlier time points.

Five separate biological replicates (i.e., each experiments was repeated five times) were obtained to collect these data for each group. PLS-DA was used to differentiate time 0 min from each of the other 7 time points (10, 20, 30, 40, 50, 60 and 75 min). This was performed in order to ascertain if the trajectory seen in FIG. 8 is statistically meaningful; that is to say could one differentiate the spectral profiles taken at time X (10, 20, 30, 40, 50, 60 and 75 min) from the initial spectra recorded at time 0 min.

Results from this analysis are shown in Table 5. These indicate that especially after antibiotic addition the models' accuracy can be greater than 90% and up to 100% by the 30 min time point.

TABLE 5

PLS-DA prediction accuracies of whether it is possible to differentiate between resistance and sensitive bacteria at each of the time points with the 0 min time point (from either sensitive or resistant) as the comparator.

| Timepoint | Prediction accuracy (%) | | | |
|---|---|---|---|---|
| | Without antibiotic addition | | With antibiotic addition | |
| (min) | Resistant | Sensitive | Resistant | Sensitive |
| 10 | 59.26 | 40.74 | 87.04 | 77.78 |
| 20 | 87.04 | 74.07 | 70.37 | 100 |
| 30 | 100 | 68.15 | 100 | 94.44 |
| 40 | 98.15 | 57.44 | 88.89 | 98.15 |

TABLE 5-continued

PLS-DA prediction accuracies of whether it is possible to differentiate between resistance and sensitive bacteria at each of the time points with the 0 min time point (from either sensitive or resistant) as the comparator.

| Timepoint | Prediction accuracy (%) | | | |
|---|---|---|---|---|
| | Without antibiotic addition | | With antibiotic addition | |
| (min) | Resistant | Sensitive | Resistant | Sensitive |
| 50 | 100 | 77.78 | 100 | 98.15 |
| 60 | 100 | 77.78 | 100 | 96.30 |
| 75 | 100 | 83.33 | 100 | 100 |

The next step was to use PLS-DA to predict resistance or sensitivity from each of the time points after exposure to the antimicrobial. That is to say at say time 10 min could the PLS-DA predict whether the spectral profile from the sensitive bacteria were significantly different from the resistant bacteria.

TABLE 6

PLS-DA prediction accuracy of antibiotic resistant and sensitive bacteria during each time point.

| Timepoint | Prediction accuracy (%) | |
|---|---|---|
| (min) | Resistant | Sensitive |
| 10 | 87.08 | 100 |
| 20 | 100 | 100 |
| 30 | 100 | 100 |
| 40 | 100 | 100 |
| 50 | 100 | 100 |
| 60 | 100 | 100 |
| 75 | 100 | 100 |

Table 6 shows excellent differentiation occurring 20 min after the addition of antibiotic. In these models the comparator is obtained at the same time point but without an antibiotic being added.

Determining Susceptibility/Resistance Using UV-Vis

Figure 9:
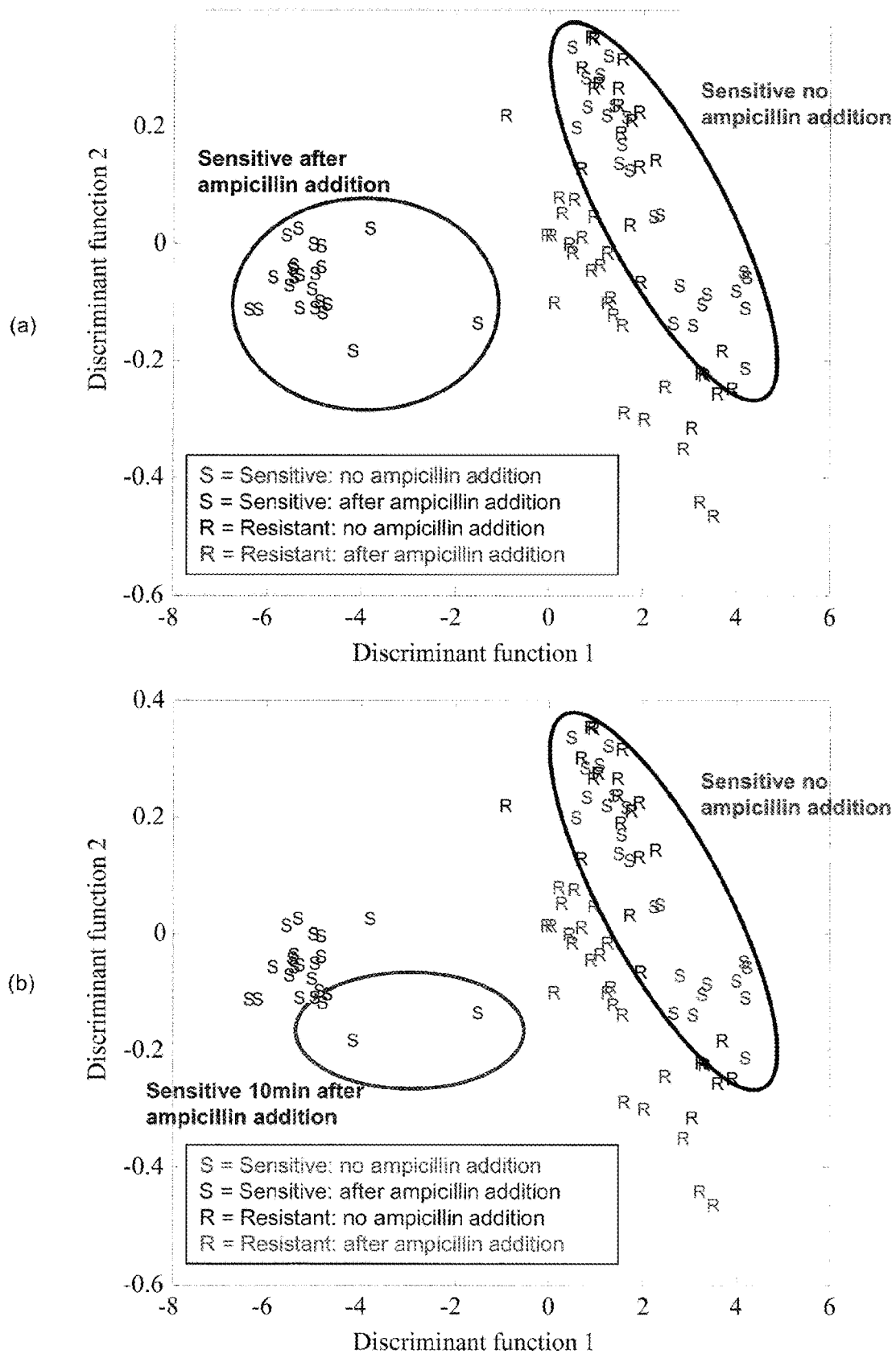
FIG. 9(a) shows Cluster plots showing the phenotypic effects on antibiotic sensitive bacterial samples ("S") and antibiotic resistant bacterial samples ("R") obtained from UV-Vis (a) as measured before addition of the ampicillin antibiotic and as measured at 10 min, 20 min, 30 min and 75 min time points after the addition of the ampicillin antibiotic.
FIG. 9(b) is the same as FIG. 9(a) but with the antibiotic sensitive as measured at 10 min after the addition of the ampicillin antibiotic being highlighted for clarity.

As shown by FIG. 9, UV-Vis is equally capable of measuring separation between bacterial samples on a cluster plot, according to whether those bacterial samples are resistant or not.

To obtain the data shown in FIG. 9, four *E. coli* isolates were used (two sensitive and two resistant), with two conditions being used for measurements (either with exposure to the antibiotic ampicillin or with no exposure to the antibiotic), with four time points (10, 20, 30 and 75 min) hence, there are thirty-two data points shown in FIG. 9 (4×2×4=32).

It is clear from this plot that even after only 10 min antibiotic exposure the bacteria that were sensitive have a very different trajectory from the bacteria that are resistant to the antimicrobial.

Testing on a Urine Samples

In a clinical environment, it may be desirable to use an uncultured sample, e.g. an uncultured urine sample in which a bacteria of interest has not be grown in an artificial culture prior to antibiotic testing. Therefore, in order to simulate the application of the methods described herein to real uncultured urine samples obtained from patients, pooled human urine from healthy volunteers was spiked with 6 well characterised UTI bacteria which were either sensitive or resistant to ampicillin. After exposure for 75 min the bacteria were analysed using FT-IR spectroscopy. The FT-IR spectra were then analysed using PLS-DA and the results from bootstrapping testing are shown in Table 7.

TABLE 7

PLS-DA accuracy values from 6 UTI isolates directly from urine before and after exposure to Ampicilin. The values shown are from five biological replicates from each isolates. These 30 samples were then analysed using bootstrapped PLS and the averages from 1000 bootstrap validation tests are shown.

| | Predicted group | | | |
|---|---|---|---|---|
| | Before antibiotic addition | | After antibiotic addition | |
| Actual group | Resistant | Sensitive | Resistant | Sensitive |
| Resistant | 82.65% | 17.35% | 93.94% | 6.06% |
| Sensitive | 15.71% | 84.29% | 7.34% | 92.66% |
| Overall accuracy | 83.47% | | 93.30% | |

Prior to the addition of antibiotic the models' predictive ability for antibiotic testing was ~83%, and after antibiotic addition the predictive accuracy improves to ~93%. This illustrates that in this urine environment the bacteria are also undergoing some changes on exposure to ampicillin which we are able to measure using FT-IR spectroscopy. Without wishing to be bound by theory, the inventors believe that the predictive ability (of ~83%) before addition of the antibiotics may be related to some intrinsic difference in the strains of *E. coli* used Experimental Work 2

In this experimental work, *E. coli* K12 MG1655 was exposed to: Cirprofloxacin at 10 mg/L (coded 'C'); Trimethoprim at 300 mg/L (coded 'T'); Ampicillin at 10 mg/L (Coded 'A'); control—no antibiotic (coded as 'O'). Post challenge (or control) UV-vis data were collected after 10, 20 and 30 min.

UV-Vis analysis in transmission mode was performed using a Thermo Biomate 5 UV-Vis spectrometer. A medium blank was used as the reference material. Samples were presented directly in liquid form within cuvettes to the instrument. The spectral range used was 300 nm to 800 nm.

Figure 10:
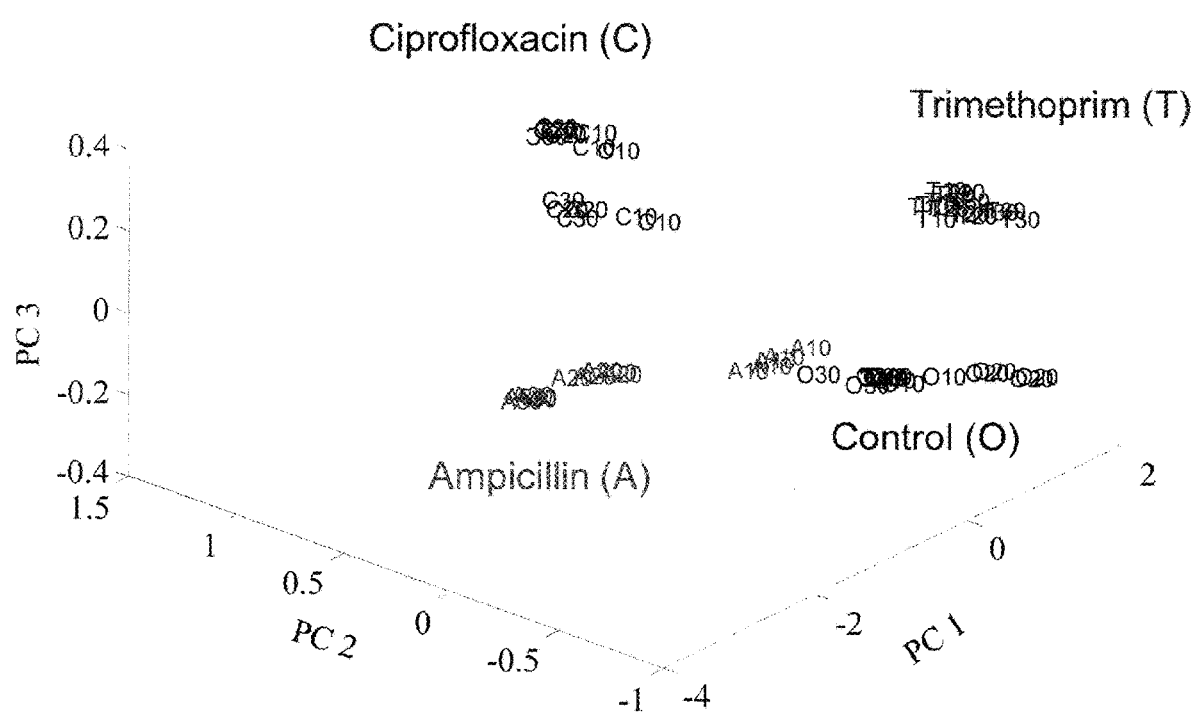
FIG. 10 shows the results of cluster analysis using principal components-discriminant function analysis (PC-DFA) constructed from UV-Vis spectra obtained from the *E. coli* K12 bacteria when exposed to pure antibiotic at 400% MIC.

The results of this analysis are shown in FIG. 10, which shows the results of cluster analysis using principal components-discriminant function analysis (PC-DFA) constructed from UV-Vis spectra obtained from the *E. coli* K12 bacteria when exposed to pure antibiotic at 400% MIC.

Experimental Work 3

In this experimental work, UV-Vis spectroscopy and PLS-DA were used with 137 *E. coli* isolates to differentiate between sensitive and resistant strains for three different antibiotics (Ampicillin, Trimethoprim, Ciprofloxacin).

Experimental Work 3

Material and Methods

Inoculum Preparation

The selected isolates (n=137) of *E. coli* were sub-cultured on nutrient agar. A single colony was taken and added to 50 mL of nutrient broth in a 250 mL conical flask, and incubated overnight at 37° C. with 200 rpm shaking.

Sample Preparation

For each strain, 3 mL of nutrient broth was inoculated with the overnight grown cells to a final $OD_{600nm}$=0.1, followed by dispensing the samples as 200 µL aliquots in a sterile Corning 96 well plate (5 biological replicates per strain for each condition). All plates were sealed using sterile Breath-Easy sealing membranes to reduce sample evaporation. The plates were incubated at 37° C. with 200 rpm shaking for 150 min. At this point the cells were exposed to one of the following conditions by adding 8 µL of 25× concentrated stock solution of; a) ampicillin, final concentration 32 mg/L, b) ciprofloxacin, final concentration 4 mg/L, c) trimethoprim, final concentration 16 mg/L and d) 0.9% sterile sodium chloride solution.

The plates were transferred to one of two BioTek Synergy HT microplate readers programmed for 30 min shaking with medium speed at 37° C. followed by a full scan (200-999 nm range) of all the samples with 2 nm resolution.

40 samples were analysed on each plate at every run to avoid any variation due to the time delay. 2× UV-vis spectrometers were used for all analyses and data were consistent irrespective of the instrument employed. This highlights the excellent reproducibility of the spectral analyses Data Processing All data were processed in Microsoft Excel to prepare the data prior to PLS-DA analysis, which was performed in Matlab. PLS-DA was used to differentiate between sensitive and resistant strains. To validate this process: (a) 10,000 bootstrap iterations were used and (b) the same 10,000 iterations were also used to construct null models by permutation of the sensitivity or resistance label. The tabulated results are the test set means from the 10,000 models.

Consumables and Instrument Used

These were:

Corning 96 well cell culture cluster (3596), Flat bottom with lid, Polystyrene, Sterile BiotTek, Synergy HT Microplate reader for HIS and drug discovery Breath-Easy sealing membranes (Sigma, Z380059-1 PAK)

All antibiotics were purchased from Sigma (Sigma Aldrich, Dorset, UK)

Experimental Work 3

Results and Discussion

The UV-Vis data included in Tables 8 and 9, shown below, are the results of an experiment testing 5 replicates of each of the 137 *E. coli* strains, 30 min after the addition of three different antibiotics.

TABLE 8

PLS-DA prediction accuracy for 137 different clinical isolates that are either sensitive or resistant to one of three different antibiotics (values in parentheses are the concentrations of antimicrobial used): ampicillin (16 mg/L), trimethoprim (32 mg/L), ciprofloxacin (4 mg/L), with UV-Vis spectroscopy being performed 30 minutes after initial exposure to the antibiotics.

| | UV-Vis (30 mins) After antibiotic addition | | |
|---|---|---|---|
| Antibiotic | Accuracy for Resistant Isolates | Accuracy for Sensitive isolates | Overall model accuracy |
| Ampicillin | 88.73% | 89.22% | 88.97% |
| Trimethoprim | 90.49% | 76.55% | 83.52% |
| Ciprofloxacin | 97.53% | 76.90% | 87.21% |

Here, it may be instructive to compare the results obtained using UV-Vis spectrometry applied 30 min after exposure of the bacteria to the antibiotic (presented using predicted accuracy values in Table 8) with the results obtained using FT-IR spectrometry applied at the longer time of 75 min after exposure of the bacteria to the antibiotic (presented using predicted accuracy values in Table 3), by comparing positive predictive values (susceptibility) scores generated from these two sets of results, as in Table 9, below.

TABLE 9

PLS-DA prediction accuracy for FT-IR as shown in Table 3 and for UV-Vis as shown in Table 7.
Positive Predictive Values (susceptibility)

|  | FT-IR (75 min) | UV-Vis (30 min) |
| --- | --- | --- |
| Ampicillin | 90.6% | 88.66% |
| Trimethoprim | 89.4% | 92.47% |
| Ciprofloxacin | 98.4% | 98.21% |

In Table 9, results are shown in the form of positive predictive values (susceptibility) which compares the number of correct indications of susceptibility made versus the total number of indications of susceptibility made (i.e. true positives/total positives). Positive predictive value (susceptibility) is a particularly useful parameter in relation to this experimental work, since a correct indication of susceptibility of a given bacterium of interest to a given antibiotic can be used in a clinical environment to identify an antibiotic for treating an infection caused by that bacterium.

Further Discussion

The UV-Vis spectrometry in Experimental Work 2 and Experimental Work 3 was performed using polystyrene microtitre plates, whereas the earlier testing in Experimental Work 1 was carried out using optical glass cuvettes, thus demonstrating that comparable performance can be achieved using UV-Vis on wet samples even when contained in polystyrene test cells versus FT-IR where the sample is dried on the sensor surface.

It also demonstrates that UV-Vis testing at short test times (30 min data shown) does not sacrifice performance.

In addition, our UV-Vis testing has been carried out using three different UV-Vis spectrometers, since Experimental Work 1 was carried out on a Thermo Biomate 5 UV-Vis spectrometer across spectral range of 300-800 nm, but Experimental Work 2 and Experimental Work 3 were run on two different BioTek Synergy HT microplate reader across wavelengths 200-999 nm.

All results are comparable with those obtained using FT-IR where the sample requires drying because of interference from the water in the sample, and where the sample cannot be contained in a plastic cuvette because of interference from IR absorption in the associated polymers.

Experimental Work 4

In the experimental work discussed above, FT-IR spectroscopy and UV-Vis spectroscopy were used on a large number (>200) of different strains of E. coli bacteria, so as to provide in depth analysis demonstrating that information regarding susceptibility/resistance of a selected bacterium to various antibiotics can be obtained from spectroscopic data obtained shortly after exposing the selected bacterium to such antibiotics.

In this experimental work, UV-Vis spectroscopy has been used with three strains of bacteria that were selected as being different from E. coli bacteria, to demonstrate that obtaining information regarding susceptibility/resistance of a selected bacterium to various antibiotics (from spectroscopic data obtained shortly after exposing the selected bacterium to such antibiotics) is not limited to use with E. coli bacteria, but can be used with a wide variety of bacteria.

The selected strains of bacteria and the antibiotics used in this experimental work are shown in Table 10, below.

TABLE 10

Selected strains of bacteria used in Experimental Work 4.

| | Selected strain of bacteria | | |
| --- | --- | --- | --- |
| Antibiotic | Staphylococcus aureus (Gram-positive) | Psuedomonas aeruginosa (Gram-negative) | Staphylococcus epidermidis (Gram-positive) |
| Ampicillin | Sensitive | Resistant | Resistant |
| Ciprofloxacin | Sensitive | Sensitive | Sensitive |
| Trimethoprim | Resistant | Resistant | Resistant |

Experimental Work 4

Material and Methods

In general, unless otherwise stated, the material and methods for Experimental Work 4 were the same as for Experimental Work 3, except that a single Thermo Biomate 5 UV-Vis spectrometer across spectral range of 300-800 nm was used for data collection in Experimental Work 4.

Experimental Work 4

Results and Discussion

The results of this experimental work will now be discussed with reference to FIGS. 11-13.

FIG. 11(a) is a cluster plot showing the results of exposing samples including the selected strain of S. aureus (resistant to Trimethoprim) to Trimethoprim, compared with control samples of the same strain that were not exposed to Trimethoprim.

In FIG. 11(a), a small shift (~4 units) in the cluster plot can be seen after 30 minutes (the shift at 10 minutes was minimal).

FIG. 11(b) is a cluster plot showing the results of exposing samples including the selected strain of P. aeruginosa (resistant to Trimethoprim) to Trimethoprim, compared with control samples of the same strain that were not exposed to Trimethoprim.

In FIG. 11(b), a small shift (~3 units) in the cluster plot can be seen after both 10 minutes and 30 minutes.

FIG. 11(c) is a cluster plot showing the results of exposing samples including the selected strain of S. epidermidis (resistant to Trimethoprim) to Trimethoprim, compared with control samples of the same strain that were not exposed to Trimethoprim.

Figure 11:
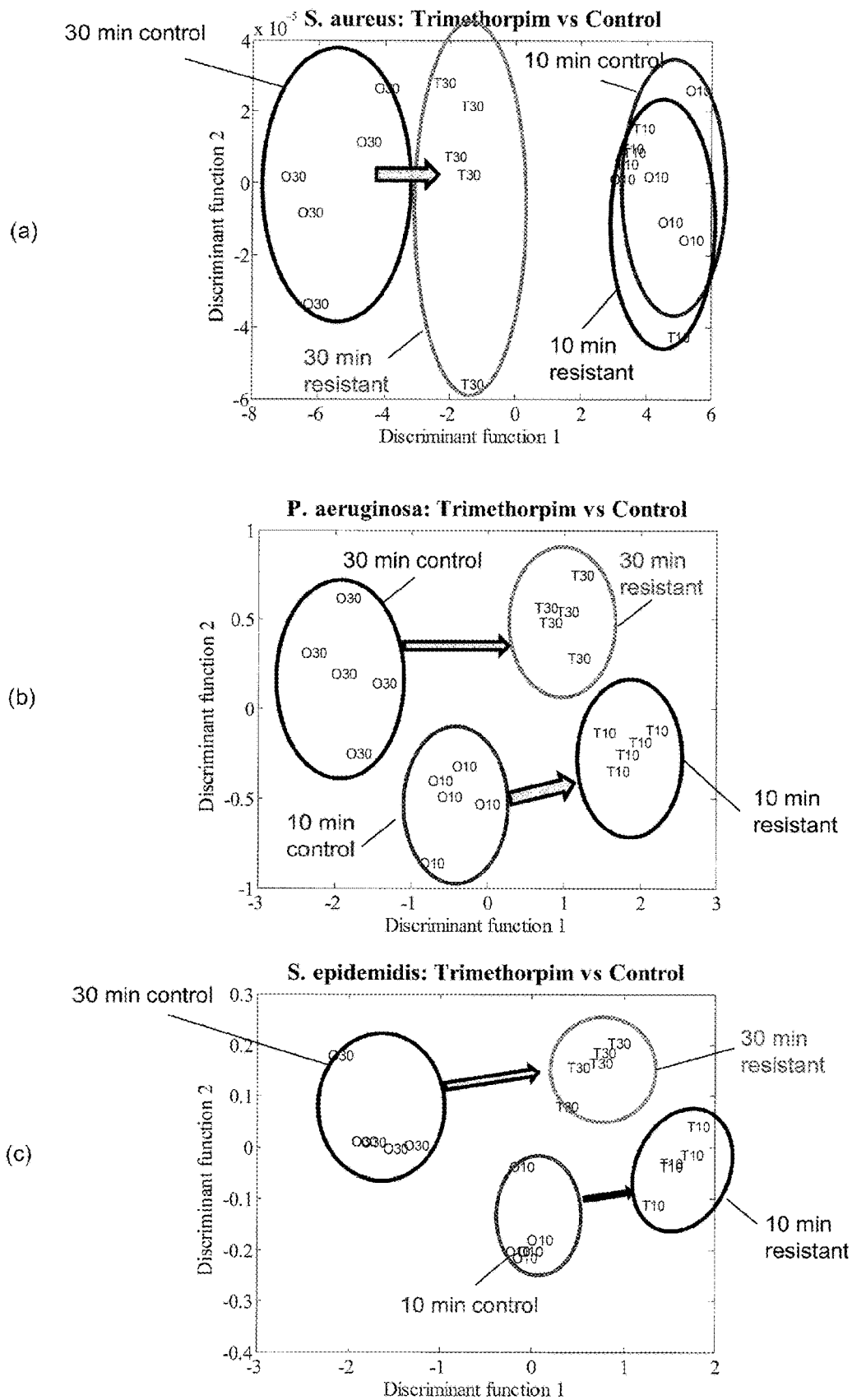
FIGS. 11(a)-11(c) shows the results of cluster analysis using principal components-discriminant function analysis (PC-DFA) constructed from UV-Vis spectra, which show the phenotypic effects on selected bacterial samples of *S. aureus, P. aeruginosa*, and *S. epidermidis* , respectively, due to Trimethoprim.

In FIG. 11 (c), a small shift (~3 units) in the cluster plot can be seen after both 10 minutes and 30 minutes.

What the data in FIG. 11 show is that on exposure to Trimethoprim (i.e. "Trimethoprim challenge") all strains show the same behaviour at 10 min and 30 min after exposure to Trimethoprim. This similar behaviour is because these three strains are all resistant to Trimethoprim and this is seen as a small shift in the PC-DFA scale on these plots.

FIG. 12(a) is a cluster plot showing the results of exposing samples including the selected strain of S. aureus (sensitive to Ciprofloxacin) to Ciprofloxacin, compared with control samples of the same strain that were not exposed to Ciprofloxacin.

In FIG. 12(a), a large shift (~100 units) in the cluster plot can be seen after both 10 minutes and 30 minutes FIG. 12(b) is a cluster plot showing the results of exposing samples including the selected strain of P. aeruginosa (sensitive to Ciprofloxacin) to Ciprofloxacin, compared with control samples of the same strain that were not exposed to Ciprofloxacin.

In FIG. 12(b), a large shift (~100 units) in the cluster plot can be seen after both 10 minutes and 30 minutes.

FIG. 12(c) is a cluster plot showing the results of exposing samples including the selected strain of S. epidemidis (sensitive to Ciprofloxacin) to Ciprofloxacin, compared with control samples of the same strain that were not exposed to Ciprofloxacin. We note that the arrows are in the opposite direction but (it is thought that) the important aspect is that the first discriminant function axis explains the most important difference and it does not matter which way round the arrow points as long as both arrows extend in a similar direction, which they clearly do.

In FIG. 12(c), a large shift (~100+units) in the cluster plot can be seen after both 10 minutes and 30 minutes.

Figure 12:
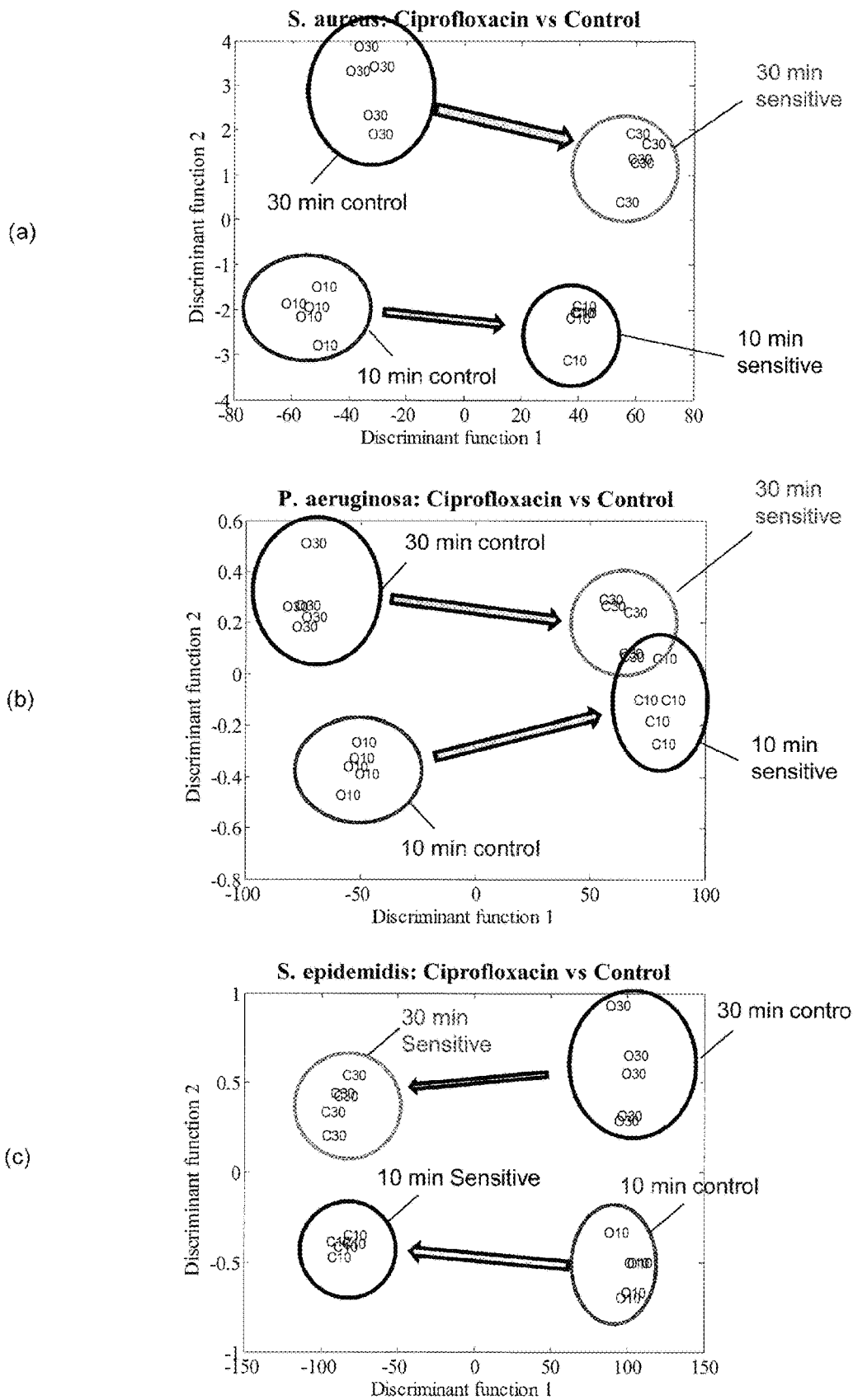
FIGS 12(a)-12(c) show the results of cluster analysis using principal components-discriminant function analysis (PC-DFA) constructed from UV-Vis spectra, which show the phenotypic effects on selected bacterial samples of *S. aureus, P. aeruginosa*, and *S. epidermidis*, respectively, due to Ciprofloxacin.

What the data in FIG. 12 show is that on exposure to Ciprofloxacin (i.e. "ciprofloxacin challenge") all strains show the same behaviour at 10 min and 30 min after exposure to Ciprofloxacin. This similar behaviour is because these three strains are all sensitive to Ciprofloxacin and this is seen as a large shift in the PC-DFA scale on these plots.

FIG. 13(a) is a cluster plot showing the results of exposing samples including the selected strain of S. aureus (sensitive to Ampicillin) to Ampicillin, compared with control samples of the same strain that were not exposed to Ampicillin.

In FIG. 13(a), a small shift (~1.5 unit) in the cluster plot can be seen after 30 minutes (the shift at 10 minutes was minimal).

FIG. 13(b) is a cluster plot showing the results of exposing samples including the selected strain of P. aeruginosa (resistant to Ampicillin) to Ampicillin, compared with control samples of the same strain that were not exposed to Ampicillin.

In FIG. 13(b), the shift at 10 minutes and 30 minutes was minimal.

FIG. 13(c) is a cluster plot showing the results of exposing samples including the selected strain of S. epidermidis (resistant to Ampicillin) to Ampicillin, compared with control samples of the same strain that were not exposed to Ampicillin.

In FIG. 13(c), the shift at 10 minutes and 30 minutes was minimal.

Figure 13:
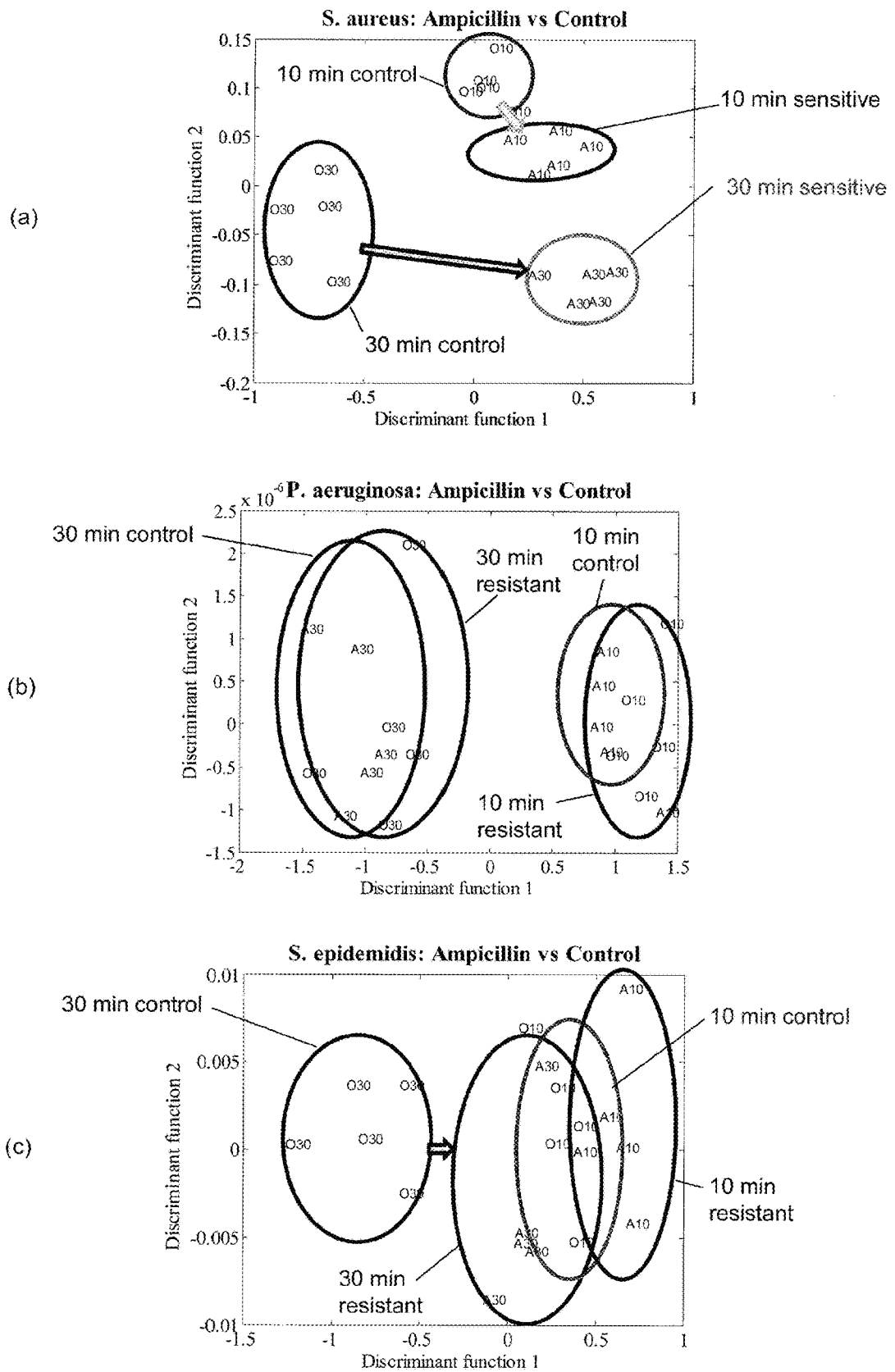
FIGS 13(a)-13(c) show the results of cluster analysis using principal components-discriminant function analysis (PC-DFA) constructed from UV-Vis spectra, which show the phenotypic effects on selected bacterial samples of *S. aureus, P. aeruginosa*, and *S. epidermidis*, respectively due to Ampicillin.

The analyses for Ampicillin shown in FIG. 13 is different from that for Trimethoprim or Ciprofloxacin (shown in FIGS. 11-12) because the strains that were analysed were a mix of being sensitive and resistant to Ampicillin. In particular, the selected strain of S. aureus was sensitive to ampicillin and so there is a clear shift on the cluster plot between the S. aureus bacteria control sample that was not exposed to Ampicillin, compared to the S. aureus bacteria sample that was exposed to Ampicillin for 10 min and 30 min. By contrast, the selected strains of P. aeruginosa and S. epidermidis were resistant to Ampicillin, and there appears to be very little shift on the cluster plot for the P. aeruginosa and S. epidermidis bacteria samples that were exposed to Ampicillin for 10 min and 30 min, compared with the P. aeruginosa and S. epidermidis bacteria control samples that were not exposed to Ampicillin.

What the above data show is that there are different phenotypic effects that are observed in UV-Vis spectrum data for bacteria of different genera and different Gram stain, depending on whether the bacterium under test is susceptible/resistant to an antimicrobial to which it has been exposed. This demonstrates that the method will work at 10 min exposure to the antibiotic for a wide range of genotypically diverse bacteria.

In view of the above, a skilled person would find no difficulty in obtaining information regarding the susceptibility/resistance of a given microorganism of interest to a given antimicrobial from spectrum data, where that spectrum data has been obtained by applying UV-Vis (or FT-IR) spectroscopy to a sample including the microorganism of interest shortly after the sample has been exposed to the given antimicrobial. In Experimental Work 1 and 3 (above), this was demonstrated for E. coli bacteria by a methodology that involved using a number of strains of E. coli bacteria (of known susceptibility/resistance) as reference bacteria to form models which were then used to determine whether other strains of E. coli bacteria were susceptible/resistant to various antibiotics. Experimental Work 4 demonstrates that a similar methodology could be applied to a diverse range of bacteria. So, for example, it would be straightforward for a skilled person to use multiple strains of S. aureus (of known susceptibility/resistance) as reference bacteria to form a model which could then be used to determine whether a given S. aureus bacterium is susceptible/resistant to a given antibiotic. However, a skilled person would readily appreciate that the methodology described in relation to Experimental Work 1 and 3 (above) is just one example methodology, and that there are a variety of possible methodologies by which information regarding the susceptibility/resistance of a given bacterium of interest to a given antibiotic can be obtained from spectrum data, e.g. as discussed in detail above in relation to the first and second aspects of this invention.

Final Remarks

When used in this specification and claims, the terms "comprises" and "comprising", "including" and variations thereof mean that the specified features, steps or integers are included. The terms are not to be interpreted to exclude the possibility of other features, steps or integers being present.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

All references referred to above are hereby incorporated by reference.

REFERENCES

1. B. Foxman, *Disease-a-month,* 2003, 49, 53-70.
2. B. Foxman, *Nature Reviews. Urology,* 2010, 7, 653-660.
3. Standards Unit Microbiology Services Division, *UK Standards for microbiology investigations. Investigation of urine,* Health Protection Agency (HPA), 2009.
4. *Management of suspected bacterial urinary tract infection in adults. A national clinical guideline,* Scottish Intercollegiate guidelines network (SIGN), 2012.
5. J. Car, *British Medical Journal,* 2006, 332, 94-97.
6. G. Kahlmeter, *Journal of antimicrobial chemotherapy,* 2003, 51, 69-76.
7. S. D. Fihn, *New England Journal of Medicine,* 2003, 349, 259-266.
8. A. Fluit and F. Schmitz, *Expert opinion in pharmacotherapy,* 2001, 2, 813-818.
9. A. Manges, J. Johnson, B. Foxman, T. O'Bryan, K. Fullerton and L. Riley, *New England Journal of Medicine,* 2001, 345, 1007-1013.
10. B. Rogers, H. Sidijabat and D. Paterson, *Journal of antimicrobial chemotherapy,* 2011, 66, 1-14.
11. R. Goodacre, E. M. Timmins, R. Burton, N. Kaderbhai, A. M. Woodward, D. B. Kell and P. J. Rooney, *Microbiology,* 1998, 144, 1157-1170.
12. K. Maquelin, L.-P. Choo-Smith, H. P. Endtz, H. A. Bruining and H. J. Puppels, *Journal of Clinical Microbiology,* 2002, 40, 594-600.
13. D. Naumann, D. Helm and H. Labinchinski, *Nature,* 1991, 351, 81-82.
14. C. L. Winder, E. Carr, R. Goodacre and R. Seviour, *Journal of Applied Microbiology,* 2004, 96, 328-339.
15. B. Stuart, *Biological Applications of Infrared Spectroscopy,* 1st edition edn., John Wiley & Sons Inc., Chichester, 1997.
16. H. AlRabiah, E. Correa, M. Upton and R. Goodacre, *Analyst,* 2013.
17. J. M. Andrews, *Journal of antimicrobial chemotherapy,* 2001, 48 S1, 5-16.
18. N. Nicolaou, Y. Xu and R. Goodacre, *Analytical chemistry,* 2011, 83, 5681-5687.
19. H. Martens, N. J. Pram and E. S. Balling, *Annals of Chemistry,* 2003, 75, 394-404.
20. R. Goodacre and D. B. Kell, in *Metabolic Profiling—Its role in biomarker dicovery and gene function analysis,* eds. G. H. Harrigan and R. Goodacre, Kluwer Academic Publishers, London, 2003, pp. 239-256.
21. I. T. Jolliffe, *Principal Component Analysis,* 1st edition edn., Springer-Verlag, New York, 1986.
22. L. Mariey, J. P. Signolle, C. Amiel and J. Travent, *Vibrational Spectroscopy,* 2001, 26, 151-159.
23. B. F. J. Manly, *Multivariate Statistical methods: a primer,* Chapman and Hall, London, 1994.
24. R. M. Jarvis and R. Goodacre, *Analytical Chemistry,* 2004, 76, 40-47.
25. D. Ballabio and R. Todeschini, in *Infrared spectroscopy for food analysis and control,* Academic Press, London, 1st edn., 2009, pp. 83-104.
26. M. Barker and W. S. Ravens, *Journal of Chemometrics,* 2003, 17, 166-173.
27. B. Efron, *Biometrika,* 1981, 68, 589-599.
28. B. Efron and R. J. Tibshirani, *An introduction to bootstrap,* Chapman & Hall/CRC, Washington D.C., 1994.
29. Goodacre, R., Timmins, É. M., Burton, R., Kaderbhai, N., Woodward, A. M., Kell, D. B. & Rooney, P. J. (1998) Rapid identification of urinary tract infection bacteria using hyperspectral, whole-organism fingerprinting and artificial neural networks. *Microbiology* 144, 1157-1170.

The invention claimed is:

1. A method of analysing a sample including a bacterium of interest, the method including:
    exposing the sample to an antibiotic;
    after exposing the sample to the antibiotic, applying an absorption-based spectroscopic technique to the sample to obtain spectrum data whose spectral profile has been influenced by exposing the sample to the antibiotic, wherein applying the absorption-based spectroscopic technique to the sample includes irradiating the sample with UV Vis radiation having wavelengths in the range 200 nm to 800 nm;
    obtaining information regarding the susceptibility/resistance of the bacterium of interest to the antibiotic from a phenotypic effect in the spectrum data caused by exposing the sample to the antibiotic;
    wherein the absorption-based spectroscopic technique is applied to the sample no more than 60 minutes after the initial exposure of the sample to the antibiotic.

2. The method according to claim 1, wherein the absorption-based spectroscopic technique is applied to the sample no more than 10 minutes after the initial exposure of the sample to the antibiotic.

3. The method according to claim 1, wherein the spectroscopic technique uses electromagnetic radiation covering 50% or more of the range 200 nm to 800 nm.

4. The method according to claim 1, wherein the sample is an uncultured sample.

5. The method according to claim 1, wherein obtaining information regarding the susceptibility/resistance of the bacterium of interest to the antibiotic from the spectrum data includes:
    using multiple data points within the spectrum data to obtain spectral profile data which represents the spectral profile of the spectrum data; and
    obtaining information regarding the susceptibility/resistance of the bacterium of interest to the antibiotic from a phenotypic effect in the spectral profile data caused by exposing the sample to the antibiotic.

6. The method according to claim 5, wherein the spectral profile data are obtained according to an unsupervised computational technique, with the multiple data points within the spectrum data being used as inputs for the unsupervised computational technique.

7. The method according to claim 5, wherein the information regarding the susceptibility/resistance of the bacterium of interest to the antibiotic is obtained from the spectral profile data by applying a model to the spectral profile data.

8. The method according to claim 7, wherein the model is a supervised model that has been produced using labelled training data.

9. The method according to claim 1, wherein the method includes:
    before and after exposing the sample to the antibiotic, applying the spectroscopic technique to the sample to obtain spectrum data whose spectral profile has been influenced by exposing the sample to the antibiotic.

10. The method according to claim 1, wherein the method includes:
    before and after exposing the sample to the antibiotic, applying the spectroscopic technique to the sample to obtain delta spectrum data whose spectral profile has been influenced by exposing the sample to the antibiotic, wherein the delta spectrum data represents post-exposure spectrum data relative to pre-exposure spectrum data.

11. The method according to claim 1, wherein the information regarding the susceptibility/resistance of the bacterium of interest to the antibiotic includes an indication of whether the bacterium is susceptible or resistant to the antibiotic.

12. The method according to claim 1, wherein the information regarding the susceptibility/resistance of the bacterium of interest to the antibiotic includes an indication of a mechanism of resistance of the bacterium to the antibiotic.

13. The method according to claim 1, wherein the sample is liquid.

14. The method according to claim 1, wherein the sample includes or derives from material obtained from a patient, wherein the material obtained from the patient includes the bacterium of interest.

15. The method according to claim 1, wherein the method includes:
   obtaining material from a patient, wherein the material includes the bacterium of interest; and
   preparing the sample using the material obtained from a patient.

16. The pre-analysis method for facilitating subsequent obtaining of information regarding the susceptibility/resistance of a bacterium of interest to an antibiotic, the pre-analysis method including:
   providing a plurality of reference samples, wherein each reference sample includes a respective reference bacterium, wherein each reference bacterium is of known susceptibility/resistance to the antibiotic and has biochemical properties which are related to those of the bacterium of interest;
   for each reference sample:
   exposing the reference sample to the antibiotic;
   after exposing the reference sample to the antibiotic, applying an absorption-based spectroscopic technique to the reference sample to obtain reference spectrum data whose spectral profile has been influenced by exposing the sample to the antibiotic; and obtaining information regarding the susceptibility/resistance of the reference bacterium to the antibiotic from a phenotypic effect in the spectrum data caused by exposing the sample to the antibiotic wherein applying the absorption-based spectroscopic technique to the antibiotic from a phenotypic effect in the spectrum data caused by exposing the sample to the antibiotic sample includes irradiating the sample with UV Vis radiation having wavelengths in the range 200 nm to 800 nm, wherein the absorption-based spectroscopic technique is applied to the reference sample no more than 60 minutes after the initial exposure of the reference sample to the antibiotic.

17. A method of analysing a sample including a bacterium of interest, the method including:
   exposing the sample to an antibiotic;
   after exposing the sample to the antibiotic, applying an absorption-based spectroscopic technique to the sample to obtain spectrum data whose spectral profile has been influenced by exposing the sample to the antibiotic, wherein applying the absorption-based spectroscopic technique to the sample includes irradiating the sample with UV Vis radiation having wavelengths in the range 200 nm to 800 nm;
   obtaining information regarding the susceptibility/resistance of the bacterium of interest to the antibiotic from a phenotypic effect in the spectrum data caused by exposing the sample to the antibiotic;
   wherein the absorption-based spectroscopic technique is applied to the sample no more than 60 minutes after the initial exposure of the sample to the antibiotic;
   wherein the spectroscopic technique uses electromagnetic radiation covering 50% or more of the range 200 nm to 800 nm;
   wherein obtaining information regarding the susceptibility/resistance of the bacterium of interest to the antibiotic from the spectrum data includes:
      using multiple data points within the spectrum data to obtain spectral profile data which represents the spectral profile of the spectrum data; and
      obtaining information regarding the susceptibility/resistance of the bacterium of interest to the antibiotic from a phenotypic effect in the spectral profile data caused by exposing the sample to the antibiotic;
   wherein the spectral profile data are obtained according to an unsupervised computational technique, with the multiple data points within the spectrum data being used as inputs for the unsupervised computational technique.

* * * * *